US009033961B2

(12) United States Patent
Melsky et al.

(10) Patent No.: US 9,033,961 B2
(45) Date of Patent: May 19, 2015

(54) CARDIAC ABLATION CATHETERS FOR FORMING OVERLAPPING LESIONS

(75) Inventors: Gerald Melsky, Lexington, MA (US);
Stephen W. Sagon, Amherst, MA (US);
Alfred Stancampiano, Waban, MA (US); Jeffrey M. Arnold, Wellesley, MA (US); Lincoln S. Baxter, Centerville, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 1275 days.

(21) Appl. No.: 12/423,178

(22) Filed: Apr. 14, 2009

(65) Prior Publication Data

US 2009/0299354 A1 Dec. 3, 2009

Related U.S. Application Data

(63) Continuation-in-part of application No. 10/357,156, filed on Feb. 3, 2003, now Pat. No. 8,025,661, which is a continuation-in-part of application No. 09/924,394, filed on Aug. 7, 2001, now Pat. No. 6,579,285, and a (Continued)

(51) Int. Cl.
*A61B 5/06* (2006.01)
*A61B 18/24* (2006.01)
(Continued)

(52) U.S. Cl.
CPC ..... *A61B 18/245* (2013.01); *A61B 2017/00057* (2013.01); *A61B 2017/00061* (2013.01);
(Continued)

(58) Field of Classification Search
USPC ..................... 606/2, 14–16, 32, 41
See application file for complete search history.

(56) References Cited

U.S. PATENT DOCUMENTS 3,417,745 A 12/1968 Sheldon
3,821,510 A 6/1974 Muncheryan
(Continued)

FOREIGN PATENT DOCUMENTS

DE 94117543 11/1994
EP 0214712 3/1987
(Continued)

OTHER PUBLICATIONS

Bredikis, J. et al. "Laser Destruction of the Atrioventricular Bundle Using the Cardiac Endoscope" Kardiologiia, 1988, 28(8): 94-96.
(Continued)

*Primary Examiner* — Aaron Roane
(74) *Attorney, Agent, or Firm* — Leason Ellis LLP

(57) ABSTRACT

Methods and instruments are disclosed for creating lesions in tissue, especially cardiac tissue, for treatment of arrhythmias and the like, by employing an elastic balloon and an energy emitter, which is independently positionable within the lumen of the instrument and adapted to project a series of spots of ablative energy through a transmissive region of the balloon to a target tissue site. The energy emitter preferably is configured such the spots of energy result in a series of lesions formed in the target tissue region when the emitter is activated, the lesions having an average area ranging from about 5 mm$^2$ to about 100 mm$^2$. In one aspect of the invention, percutaneous ablation instruments are disclosed in the form of catheter bodies having one or more balloon structures at the distal end region of the instrument and an energy emitting element, which is independently positionable and rotatable within a lumen of the instrument and adapted to project ablative energy through a transmissive region of the balloon to a target tissue site in contact with, or proximal to, the balloon surface.

18 Claims, 9 Drawing Sheets

Related U.S. Application Data continuation-in-part of application No. 09/616,275, filed on Jul. 14, 2000, now Pat. No. 6,626,900, which is a continuation-in-part of application No. 09/602,420, filed on Jun. 23, 2000, now Pat. No. 6,572,609, which is a continuation-in-part of application No. 09/357,355, filed on Jul. 14, 1999, now Pat. No. 6,423,055.

(51) Int. Cl.

| A61B 17/00 | (2006.01) |
|---|---|
| A61B 18/00 | (2006.01) |
| A61B 18/22 | (2006.01) |
| A61B 19/00 | (2006.01) |
| A61N 7/02 | (2006.01) |

(52) U.S. Cl.
CPC . *A61B2018/0097* (2013.01); *A61B 2018/2261* (2013.01); *A61B 2018/2266* (2013.01); *A61B 2018/2272* (2013.01); *A61B 2019/465* (2013.01); *A61N 7/02* (2013.01)

(56) References Cited

U.S. PATENT DOCUMENTS

| | | |
|---|---|---|
| 4,224,929 A | 9/1980 | Furihata et al. |
| 4,233,493 A | 11/1980 | Nath et al. |
| 4,273,109 A | 6/1981 | Enderby |
| 4,336,809 A | 6/1982 | Clark |
| 4,445,892 A | 5/1984 | Hussein et al. |
| 4,585,298 A | 4/1986 | Mori et al. |
| 4,625,724 A | 12/1986 | Suzuki et al. |
| 4,660,925 A | 4/1987 | McCaughan, Jr. |
| 4,701,166 A | 10/1987 | Groshong et al. |
| 4,718,417 A | 1/1988 | Kittrell et al. |
| 4,770,653 A | 9/1988 | Shturman |
| 4,781,681 A | 11/1988 | Sharrow et al. |
| 4,819,632 A | 4/1989 | Davies et al. |
| 4,842,390 A | 6/1989 | Sottini et al. |
| 4,852,567 A | 8/1989 | Sinofsky |
| 4,860,743 A | 8/1989 | Abela |
| 4,862,886 A | 9/1989 | Clarke et al. |
| 4,878,492 A | 11/1989 | Sinofsky et al. |
| 4,878,725 A | 11/1989 | Hessel et al. |
| 4,913,142 A | 4/1990 | Kittrell et al. |
| 4,961,738 A | 10/1990 | Mackin |
| 5,026,367 A | 6/1991 | Leckrone et al. |
| 5,030,201 A | 7/1991 | Palestrant |
| 5,053,033 A | 10/1991 | Clarke |
| 5,071,417 A | 12/1991 | Sinofsky |
| 5,078,681 A | 1/1992 | Kawashima et al. |
| 5,090,959 A | 2/1992 | Samson et al. |
| 5,109,859 A | 5/1992 | Jenkins |
| 5,125,925 A | 6/1992 | Lundahl |
| 5,133,709 A | 7/1992 | Prince |
| 5,140,987 A | 8/1992 | Schuger et al. |
| 5,151,096 A | 9/1992 | Khoury |
| 5,151,097 A | 9/1992 | Daikuzono et al. |
| 5,163,935 A | 11/1992 | Black et al. |
| 5,169,395 A | 12/1992 | Narciso, Jr. |
| 5,188,632 A | 2/1993 | Goldenberg |
| 5,188,634 A * | 2/1993 | Hussein et al. ............... 606/14 |
| 5,190,538 A | 3/1993 | Hussein et al. |
| 5,196,005 A | 3/1993 | Doiron et al. |
| 5,207,699 A | 5/1993 | Coe |
| 5,209,748 A | 5/1993 | Daikuzono et al. |
| 5,219,346 A | 6/1993 | Wagnieres et al. |
| 5,242,438 A | 9/1993 | Saadatmanesh et al. |
| 5,261,904 A | 11/1993 | Baker et al. |
| 5,269,777 A | 12/1993 | Doiron et al. |
| RE34,544 E | 2/1994 | Spears |
| 5,318,024 A | 6/1994 | Kittrell et al. |
| 5,330,465 A | 7/1994 | Doiron et al. |
| 5,337,381 A | 8/1994 | Biswas et al. |
| 5,350,375 A | 9/1994 | Deckelbaum et al. |
| 5,363,458 A | 11/1994 | Pan et al. |
| 5,368,564 A | 11/1994 | Savage |
| 5,374,953 A | 12/1994 | Sasaki et al. |
| 5,380,316 A | 1/1995 | Aita et al. |
| 5,380,317 A | 1/1995 | Everett et al. |
| 5,395,362 A | 3/1995 | Sacharoff et al. |
| 5,401,270 A | 3/1995 | Muller et al. |
| 5,409,483 A * | 4/1995 | Campbell et al. ............... 606/15 |
| 5,417,653 A | 5/1995 | Sahota et al. |
| 5,418,649 A | 5/1995 | Igarashi et al. |
| 5,423,805 A | 6/1995 | Brucker et al. |
| 5,427,119 A | 6/1995 | Swartz et al. |
| 5,431,647 A | 7/1995 | Purcell, Jr. et al. |
| 5,437,660 A | 8/1995 | Johnson et al. |
| 5,441,497 A | 8/1995 | Narciso, Jr. |
| 5,445,608 A | 8/1995 | Chen et al. |
| 5,464,404 A | 11/1995 | Abela et al. |
| 5,482,037 A | 1/1996 | Borghi et al. |
| 5,496,305 A | 3/1996 | Kittrell et al. |
| 5,497,774 A | 3/1996 | Swartz et al. |
| 5,507,725 A | 4/1996 | Savage et al. |
| 5,531,664 A | 7/1996 | Adachi et al. |
| 5,536,265 A | 7/1996 | van den Bergh et al. |
| 5,575,766 A | 11/1996 | Swartz et al. |
| 5,605,162 A | 2/1997 | Mirzaee et al. |
| 5,613,965 A | 3/1997 | Muller |
| 5,643,253 A | 7/1997 | Baxter et al. |
| 5,649,923 A | 7/1997 | Gregory et al. |
| 5,662,712 A | 9/1997 | Pathak et al. |
| 5,680,860 A | 10/1997 | Imran |
| 5,690,611 A | 11/1997 | Swartz et al. |
| 5,693,043 A | 12/1997 | Kittrell et al. |
| 5,700,243 A | 12/1997 | Narciso, Jr. |
| 5,702,438 A | 12/1997 | Avitall |
| 5,722,401 A | 3/1998 | Pietroski et al. |
| 5,725,522 A | 3/1998 | Sinofsky |
| 5,759,619 A | 6/1998 | Jin et al. |
| 5,769,843 A | 6/1998 | Abela et al. |
| 5,772,590 A | 6/1998 | Webster, Jr. |
| 5,773,835 A | 6/1998 | Sinofsky |
| 5,779,646 A | 7/1998 | Koblish et al. |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,823,955 A | 10/1998 | Kuck et al. |
| 5,824,005 A | 10/1998 | Motamedi et al. |
| 5,830,209 A | 11/1998 | Savage et al. |
| 5,833,682 A | 11/1998 | Amplatz et al. |
| 5,843,073 A | 12/1998 | Sinofsky |
| 5,845,646 A | 12/1998 | Lemelson |
| 5,860,974 A | 1/1999 | Abele |
| 5,885,278 A | 3/1999 | Fleischman |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,931,834 A | 8/1999 | Murphy-Chutorian et al. |
| 5,938,660 A | 8/1999 | Swartz et al. |
| 5,947,959 A | 9/1999 | Sinofsky |
| 5,967,984 A | 10/1999 | Chu et al. |
| 5,971,983 A | 10/1999 | Lesh |
| 5,995,875 A | 11/1999 | Blewett et al. |
| 6,004,269 A | 12/1999 | Crowley et al. |
| 6,012,457 A | 1/2000 | Lesh |
| 6,024,740 A | 2/2000 | Lesh et al. |
| 6,056,744 A | 5/2000 | Edwards |
| 6,064,902 A | 5/2000 | Haissaguerre et al. |
| 6,071,279 A | 6/2000 | Whayne et al. |
| 6,071,281 A | 6/2000 | Burnside et al. |
| 6,071,282 A | 6/2000 | Fleischman |
| 6,071,302 A | 6/2000 | Sinofsky et al. |
| 6,086,581 A | 7/2000 | Reynolds et al. |
| 6,090,084 A | 7/2000 | Hassett et al. |
| 6,099,514 A | 8/2000 | Sharkey et al. |
| 6,102,905 A | 8/2000 | Baxter et al. |
| 6,117,071 A | 9/2000 | Ito et al. |
| 6,117,101 A | 9/2000 | Diederich et al. |
| 6,120,496 A | 9/2000 | Whayne et al. |

(56) References Cited

U.S. PATENT DOCUMENTS

| | | | |
|---|---|---|---|
| 6,146,379 A | 11/2000 | Fleischman et al. |
| 6,159,203 A | 12/2000 | Sinofsky |
| 6,161,543 A | 12/2000 | Cox et al. |
| 6,164,283 A | 12/2000 | Lesh |
| 6,179,835 B1 | 1/2001 | Panescu et al. |
| 6,214,002 B1 | 4/2001 | Fleischman et al. |
| 6,217,510 B1 | 4/2001 | Ozawa et al. |
| 6,235,025 B1 | 5/2001 | Swartz et al. |
| 6,237,605 B1 | 5/2001 | Vaska et al. |
| 6,240,231 B1 | 5/2001 | Ferrera et al. |
| 6,245,064 B1 | 6/2001 | Lesh et al. |
| 6,251,092 B1 | 6/2001 | Qin et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,312,427 B1 | 11/2001 | Berube et al. |
| 6,314,962 B1 | 11/2001 | Vaska et al. |
| 6,325,797 B1 | 12/2001 | Stewart et al. |
| 6,352,531 B1 | 3/2002 | O'Connor et al. |
| 6,383,151 B1 | 5/2002 | Diederich et al. |
| 6,394,949 B1 | 5/2002 | Crowley et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,485,485 B1 | 11/2002 | Winston et al. |
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,522,933 B2 | 2/2003 | Nguyen |
| 6,544,262 B2 | 4/2003 | Fleischman |
| 6,547,780 B1 | 4/2003 | Sinofsky |
| 6,554,794 B1 | 4/2003 | Mueller et al. |
| 6,558,375 B1 | 5/2003 | Sinofsky et al. |
| 6,562,020 B1 | 5/2003 | Constantz et al. |
| 6,572,609 B1 | 6/2003 | Farr et al. |
| 6,579,278 B1 | 6/2003 | Bencini |
| 6,579,285 B2 | 6/2003 | Sinofsky |
| 6,582,536 B2 | 6/2003 | Shimada |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,648,875 B2 | 11/2003 | Simpson et al. |
| 6,669,655 B1 | 12/2003 | Acker et al. |
| 6,676,656 B2 | 1/2004 | Sinofsky |
| 6,679,873 B2 | 1/2004 | Rabiner et al. |
| 6,702,780 B1 | 3/2004 | Gilboa et al. |
| 6,771,996 B2 | 8/2004 | Bowe et al. |
| 6,896,673 B2 | 5/2005 | Hooven |
| 6,907,298 B2 | 6/2005 | Smits et al. |
| 6,916,306 B1 | 7/2005 | Jenkins et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,997,924 B2 | 2/2006 | Schwartz et al. |
| 7,207,984 B2 | 4/2007 | Farr et al. |
| 7,357,796 B2 | 4/2008 | Farr et al. |
| 7,935,108 B2 | 5/2011 | Baxter et al. |
| 8,025,661 B2 | 9/2011 | Arnold et al. |
| 2001/0030107 A1 | 10/2001 | Simpson |
| 2002/0019627 A1 | 2/2002 | Maguire et al. |
| 2002/0029062 A1 | 3/2002 | Satake |
| 2002/0065512 A1 | 5/2002 | Fjield et al. |
| 2002/0091383 A1 | 7/2002 | Hooven |
| 2002/0107511 A1 | 8/2002 | Collins et al. |
| 2002/0115995 A1 | 8/2002 | Lesh et al. |
| 2002/0120264 A1 | 8/2002 | Crowley et al. |
| 2002/0183729 A1 | 12/2002 | Farr et al. |
| 2002/0183739 A1 | 12/2002 | Long |
| 2003/0050632 A1 | 3/2003 | Fjield et al. |
| 2003/0065307 A1 | 4/2003 | Lesh |
| 2003/0069620 A1 | 4/2003 | Li |
| 2003/0111085 A1 | 6/2003 | Lesh |
| 2003/0120270 A1 | 6/2003 | Acker |
| 2003/0144657 A1 | 7/2003 | Bowe et al. |
| 2003/0158550 A1 | 8/2003 | Ganz et al. |
| 2003/0171746 A1 | 9/2003 | Fleischman |
| 2004/0006333 A1 | 1/2004 | Arnold et al. |
| 2004/0054360 A1 | 3/2004 | Schwartz et al. |
| 2004/0059397 A1 | 3/2004 | Sinofsky et al. |
| 2004/0122290 A1 | 6/2004 | Irion et al. |
| 2005/0038419 A9 | 2/2005 | Arnold et al. |
| 2005/0065504 A1 | 3/2005 | Melsky et al. |
| 2005/0222558 A1 | 10/2005 | Baxter et al. |
| 2005/0234436 A1 | 10/2005 | Baxter et al. |
| 2005/0288654 A1 | 12/2005 | Nieman et al. |
| 2006/0253113 A1 | 11/2006 | Arnold et al. |
| 2007/0078451 A1 | 4/2007 | Arnold et al. |
| 2008/0039746 A1 | 2/2008 | Hissong et al. |
| 2008/0108870 A1 | 5/2008 | Wiita et al. |
| 2008/0195088 A1 | 8/2008 | Farr et al. |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |

FOREIGN PATENT DOCUMENTS

| | | |
|---|---|---|
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9634646 | 11/1996 |
| WO | WO 9640342 | 12/1996 |
| WO | WO 9737714 | 10/1997 |
| WO | WO 00/67656 | 11/2000 |
| WO | WO 00/67832 | 11/2000 |
| WO | WO 01/03599 A2 | 1/2001 |
| WO | WO 0113812 | 3/2001 |
| WO | WO 01/64123 | 9/2001 |
| WO | WO 02/096479 | 12/2002 |
| WO | WO 03090835 | 11/2003 |
| WO | WO 2004-110258 | 12/2004 |

OTHER PUBLICATIONS

Chevalier, P. et al. "Thoracoscopic Epicardial Radiofrequency Ablation for Vagal Atrial Fibrillation in Dogs" PACE, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. et al. "Direct In Vivo Visualization of Right Cardiac Anatomy by Fiberoptic Endoscopy" Angiology; 1995, 46 (3): 201-208.

Fujimura, O. et al. "Direct In Vivo Visualization of Right Cardiac Anatomy by Fiberoptic Endoscopy: Observation of Radiofrequency-

(56) References Cited

OTHER PUBLICATIONS

Induced Acute Lesions Around the Ostium of the Coronary Sinus" European Heart J., 1994, 15: 534-540.

Gamble, W. and Innis, R. "Experimental Intracardiac Visualization" NEJM, 1967, 276(25): 1397-1403.

Hirao, K. et al. "Transcatheter Neodymium-Yttrium-Aluminum-Garnet Laser Coagulation of Canine Ventricle Using a Balloon-Tipped Cardioscope" Jpn Circ J., 1997, 61: 695-703.

Keane, D. et al. "Pulmonary Vein Isolation for Atrial Fibrillation" Rev Cardiovasc Med., 2002, 3(4): 167-175.

Kuo, C. et al. "In Vivo Angioscopic Visualization of Right Heart Structure in Dogs by Means of a Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Noncontact, Pulsed Nd:YAG Laser Using Saline Inflated Balloon Catheter," Presentation JACC 1998; 31: 118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A., et al. "Optical Properties of Circulating Human Blood in the Wavelength Range 400-2400 nm" J Biomedical Optics, 1999, 4(1): 36-46.

Saliba, W. et al. "Circumferential Ultrasound Ablation for Pulmonary Vein Isolation: Analysis of Acute and Chronic Failures" J Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D., et al. "Fiberoptic Angioscopy: Role in the Diagnosis of Chronic Pulmonary Arterial Obstruction" Ann Int Med., 1985, 103: 844-850.

Tanabe, T. et al. "Cardiovascular Fiberoptic Endoscopy: Development and Clinical Application" Surgery, 1980, 87(4): 375-379.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11: 143-148.

Vanermen, H. et al. "Minimally Invasive Video-Assisted Mitral Valve Surgery: From Port-Access Towards a Totally Endoscopic Procedure" J Card Surg., 2000, 15: 51-60.

Yamamoto, N et al. "Nonfluoroscopic Guidance for Catheter Placement into the Coronary Sinus under Direct Vision Using a Balloon-Tipped Cardioscope" PACE, 1998; 21: 1724-1729.

\* cited by examiner

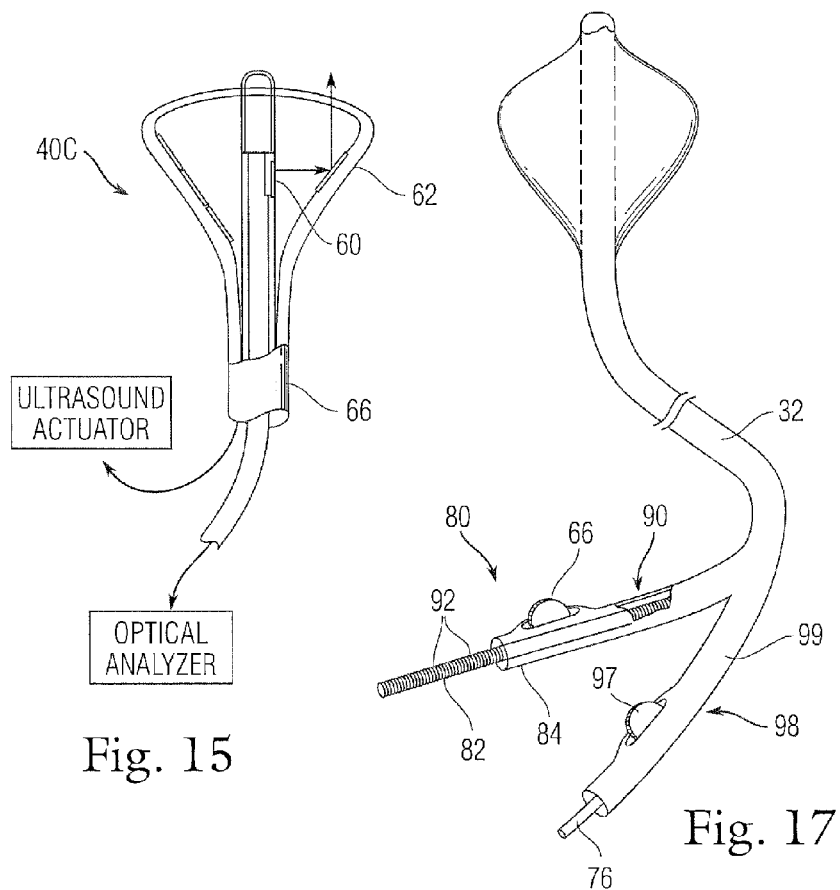
Fig. 15
Fig. 17
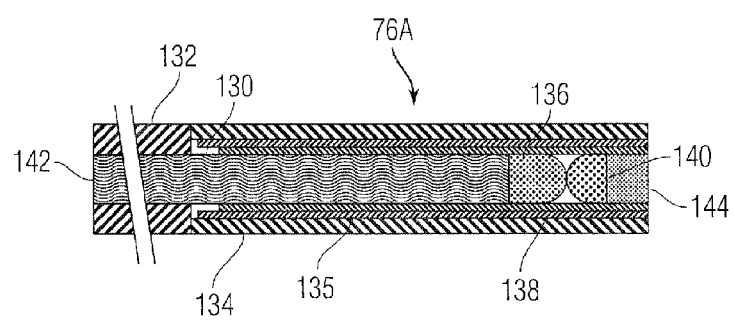
Fig. 16

CARDIAC ABLATION CATHETERS FOR FORMING OVERLAPPING LESIONS

REFERENCE TO RELATED APPLICATIONS

This application is a continuation-in-part of U.S. patent application Ser. No. 10/357,156, filed on Feb. 3, 2003 now U.S. Pat. No. 8,025,661, issued Sep. 27, 2011, which is a continuation-in-part of U.S. patent application Ser. No. 09/924,394, filed on Aug. 7, 2001, now U.S. Pat. No. 6,579,285 issued Jun. 17, 2003. Additionally, U.S. patent application Ser. No. 10/357,156 is a continuation-in-part of U.S. patent application Ser. No. 09/616,275, filed on Jul. 14, 2000, now U.S. Pat. No. 6,626,900 issued Sep. 30, 2003, which is a continuation-in-part of U.S. patent application Ser. No. 09/602,420 filed on Jun. 23, 2000, now U.S. Pat. No. 6,572,609 issued Jun. 3, 2003 which is a continuation-in-part of U.S. patent application Ser. No. 09/357,355, filed on Jul. 14, 1999, now U.S. Pat. No. 6,423,055 issued Jul. 23, 2002. The teachings of all of these prior related applications are hereby expressly incorporated by reference.

BACKGROUND OF THE INVENTION

The present disclosure relates to ablation instruments and methods of use thereof, in particular to ablation catheters and methods for the treatment of atrial fibrillation.

Cardiac arrhythmias, e.g., fibrillation, are irregularities in the normal beating pattern of the heart and can manifest themselves in either the atria or the ventricles of the heart. For example, atrial fibrillation is a form of arrhythmia characterized by rapid randomized contractions of atrial myocardium, causing an irregular, often rapid ventricular rate. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

Effective catheter treatment of atrial fibrillation was made possible by a breakthrough discovery in the late 1990's by investigators in Bordeaux, France. They found that recurrent atrial fibrillation (paroxysmal and persistent) is triggered by rapidly firing tissue, (called "ectopic foci"), that are located in one or more of the four pulmonary veins, which attach to the rear of the left atrium. Their research, since confirmed by others, suggested that 85% or more of the ectopic foci that initiate atrial fibrillation are located in or at the ostium, (mouth), of the pulmonary veins. They demonstrated that atrial fibrillation could be cured by electrically isolating the pulmonary veins from the rest of the atrium.

Various techniques have been proposed for pulmonary vein isolation. Although these procedures were originally performed with a scalpel, various other techniques have also been developed to form lesions. Collectively, these treatments are referred to as "ablation." In non-surgical ablations, the tissue is treated, generally with heat or cold, to cause coagulation and/or tissue necrosis (i.e., cell destruction). In each of these techniques, cardiac muscle cells are replaced with scar tissue which cannot conduct normal electrical activity within the heart.

In one known approach, circumferential ablation of tissue within the pulmonary veins or at the ostia of such veins has been practiced to treat atrial fibrillation. By ablating the heart tissue at selected locations, electrical conductivity from one segment to another can be blocked and the resulting segments become too small to sustain the fibrillatory process on their own.

Several types of ablation devices have recently been proposed for creating lesions to treat cardiac arrhythmias, including devices which employ electrical current (e.g., radio-frequency ("RF")) heating or cryogenic cooling. Such ablation devices have been proposed to create elongated lesions that extend through a sufficient thickness of the myocardium to block electrical conduction. Many of the recently proposed ablation instruments are percutaneous devices that are designed to create such lesions from within the heart. Such devices are positioned in the heart by catheterization of the patient, e.g., by passing the ablation instrument into the heart via a blood vessel, such as the femoral vein.

Devices that rely upon resistive or conductive heat transfer can be prone to serious post-operative complications. In order to quickly perform an ablation with such "contact" devices, a significant amount of energy must be applied directly to the target tissue site. In order to achieve transmural penetration, the surface that is contacted will experience a greater degree of heating (or freezing). For example, in RF heating of the heart wall, a transmural lesion requires that the tissue temperature be raised to about 50° C. throughout the thickness of the wall. To achieve this, the temperature at the contact surface will typically be raised to greater than 100° C. In this temperature regime, there is a substantial risk of tissue destruction (e.g., due to water vaporization micro-explosions or due to carbonization). Charring of the surface of the heart tissue, in particular, can lead to the creation of blood clots on the surface and post-operative complications, including stroke. Even if structural damage is avoided, the extent of the lesion (i.e., the width of the ablated zone) on the surface that has been contacted will typically be greater than necessary.

Cardiac ablation instruments also suffer from a variety of design limitations. For example, the shape of the heart muscle adds to the difficulty in accessing cardiac structures, such as the pulmonary veins on the anterior surface of the heart. Typically, percutaneous devices are positioned with the assistance of a guide wire, which is first advanced into heart. In one common approach, described, for example, in U.S. Pat. No. 6,012,457 issued to Lesh on Jan. 11, 2000 and in International Application Pub. No. WO 00/67656 assigned to Atrionix, Inc., a guide wire or similar guide device is advanced through the left atrium of the heart and into a pulmonary vein. A catheter instrument with an expandable element is then advanced over the guide wire and into the pulmonary vein where the expandable element (e.g., a balloon) is inflated. The balloon includes a circumferential ablation element, e.g., an RF electrode, carried on the outer surface of the balloon, which performs the ablation procedure. The balloon must be large enough and sufficiently rigid to hold the electrode in contact with the inner surface of the pulmonary vein for the length of the procedure. Moreover, because the lesion is formed by an ablation element carried on the surface of the balloon element, the balloon shape inherently limits the locations where a lesion can be formed, i.e., the lesion must be formed at least partially within the pulmonary vein.

In another approach described in U.S. Pat. No. 6,235,025 issued to Swartz et al. on May 22, 2001, a guide wire is again used to percutaneously access a pulmonary vein and a catheter is again slid over the guide wire to a position within the pulmonary vein. The catheter device includes two spaced-apart balloons, which are inflated in the vein (or in the vein and at its mouth). The space between the two balloons can then be filled with a conductive fluid to delivery RF energy (or, alternatively, ultrasound) to the vein and thereby induce a conduction block in the blood vessel by tissue ablation. With the Swartz et al. device, like the Lesh device, the region where tissue ablation can occur is limited by the design. Because two balloons must seal a space that is then filled with an ablative fluid, the lesion is necessarily formed within the pulmonary vein.

Ablation within the pulmonary vein can result in complications. Overtreatment deep within a vein can result in stenosis (closure of the vein itself), necrosis or other structural damage, any of which can necessitate immediate open chest surgery.

A limitation of these commonly utilized instruments is the lack of site selectability. Practically speaking, each such percutaneous instrument is inherently limited by its design to forming an ablative lesion at one and only one location. For example, when an expandable balloon carrying an RF heating device on its surface is deployed at the mouth of a vein, the lesion can only be formed at a location defined by the geometry of the device. It is not possible to form the lesion at another location because the heating element must contact the target tissue. Similarly, the above-described tandem balloon device can only form a lesion at a location defined by the space between the balloons that is filled with the ablative fluid.

Another limitation of such known instruments and methods is their inability to accommodate the varied geometry of the heart. For example, the inner surface of the atrium is not regular. In particular, the mouths of the pulmonary veins do not exhibit regularity; they often bear little resemblance to conical or funnel-shaped openings. Thus, when the above-described expandable, contact heating devices encounter an irregularly-shaped ostia, the result can be an incompletely formed (non-circumferential) lesion.

Moreover, the size or shape of the pulmonary vein ostia that are encountered may be too big or too small for the selected balloon catheter and it may be necessary to remove the first balloon catheter from the patient and replace it with another instrument having a balloon element of a different size. Replacement of the catheter with another before a procedure can begin (or in the middle of a multiple vein ablation protocol) can substantially increase the overall duration of the procedure and/or increase the chance of trauma.

Accordingly, there exists a need for better cardiac ablation instruments that can quickly and effective create pulmonary vein encircling lesions even in the face of irregularly shaped or variable sized target tissue regions.

SUMMARY OF THE INVENTION

Methods and instruments are disclosed for creating lesions in tissue, especially cardiac tissue, for treatment of arrhythmias and the like, by employing an elastic balloon and an energy emitter, which is independently positionable within the lumen of the instrument and adapted to project a series of spots of ablative energy through a transmissive region of the balloon to a target tissue site. The energy emitter preferably is configured such that the spots of energy result in a series of lesions formed in the target tissue region when the emitter is activated, the lesions having an average area ranging from about 5 mm$^2$ to about 100 mm$^2$ and, in some instances, 10 mm$^2$ to about 80 mm$^2$. In certain embodiments, the energy emitter is also be configured to form arc shaped lesions in the target tissue region, each arc shaped lesion subtending an angle ranging from about 5 degrees to about 45 degrees, preferably less than 30 degrees relative to the rotatable emitter (e.g., based on the emitter or longitudinal axis of optical element serving as the center of a circular frame of reference).

In one aspect of the invention, percutaneous ablation instruments are disclosed in the form of catheter bodies having one or more balloon structures at the distal end region of the instrument. The balloon structure and catheter bodies are at least partially transmissive to ablative energy. The instruments can further include an energy emitting element, which is independently positionable and rotatable within the lumen of the instrument and adapted to project ablative energy through a transmissive region of the balloon to a target tissue site in contact with the balloon surface. The energy is delivered without the need for contact between the energy emitter and the target tissue because the methods and devices of the present invention do not rely upon conductive or resistive heating. Because the position of the radiant energy emitter can be varied, the clinician can select the location of the desired lesion.

The present invention provides a mechanism for addressing the problem of instrument orientation and/or irregularly-shaped pulmonary veins by rotation and, in some instances, adjustment of the location of the energy emitter to form a series of spot lesions that overlap and create a circumferential block. For example, the devices of the present invention can form a first series of lesions along a first arc when the energy emitter is in a first location and a second series of lesions along a second arc when the energy emitter is in a second location. The spot lesions can be combined to form a continuous encircling or circumscribing lesion that blocks fibrillation-inducing electric conduction.

In another aspect of the invention, spot lesions are formed by applying radiant energy to target tissue in a range from about 50 Joules/cm$^2$ to about 1000 Joules/cm$^2$, or preferably from about 75 Joules/cm$^2$ to about 750 Joules/cm$^2$ In certain embodiments, the power levels applied by the energy emitter can range from about 10 Watts/cm$^2$ to about 150 Watts/cm$^2$ and the duration of energy delivery can range from about 1 second to about 1 minute, preferably from about 5 seconds to about 45 seconds, or more preferably from about 10 to about 30 seconds. For example, for power levels between 10 and 75 Watts/cm$^2$ it can be advantageous to apply the radiant energy for about 30 seconds. Lesser durations, e.g., of 10-20 seconds can be used for power levels of 75 to 150 Watts/cm$^2$.

In another aspect of the invention the balloon structure is a compliant balloon that is designed and configured to at least partially conform to the shape of the target tissue region upon expansion. For example, the balloon structure can be an elastic balloon (or balloon portion) configured to expand to cover pulmonary vein ostia of various sizes and/or shapes when filled with an inflation fluid. The balloon structure can also be blunt-nosed or include a tapered distal portion to help stabilize the balloon in the vein while still achieving contact with the ostial region of the vein.

In a further aspect of the invention, the percutaneous catheters of the present invention can also include a reflection sensor, such as an endoscope positionable in the instrument's distal end region to obtain an image. The image allows the clinician to visualize the anatomy of the vein, the location of side branches and the position of the instrument relative to the vein. The clinician can determine whether contact has been achieved (or blood has been cleared from an ablative energy transmission path) and the optimum location for ablation or radiation dosing before ablation begins or while ablation is occurring.

In one embodiment, percutaneous ablation catheters are disclosed having at least one central lumen and one or more compliant balloon structures at the distal end region of the instrument. Also disposed in the distal end region is an illuminating light source and an endoscope capable of collecting sufficient light to relay an image to the user. The instruments can further include one or more energy emitting elements, which are preferably independently positionable within the lumen of the instrument (e.g., along a longitudinal axis of the balloon) and adapted to project ablative energy through a transmissive region of the instrument body (and/or balloon) to a target tissue site. The energy can be delivered without the need for contact between the energy emitter and the target tissue so long as a clear transmission pathway (e.g., through the fluid of the inflated balloon) is established. The endoscope element of the instrument allows the clinician to see if such a pathway is clear.

Moreover, when the position of the radiant energy emitter can be varied, endoscopic guidance permits the clinician to select a desired location and dose for the lesion. Endoscopic inspection thus permits the clinician to define a priori an "ablation plan" before creating an overlapping series of spot lesions. Based on the locations and sizes of the lesions, the present inventions permits the user to select a suitable energy level, e.g., to compensate for the power changes due to the size of the lesion and/or to compensate for the amount of attenuation caused by projecting energy to a target site across a greater distance.

In another aspect of the invention, generally applicable to a wide range of cardiac ablation instruments, mechanisms are disclosed for determining whether the instrument has been properly seated within the heart, e.g., whether the device is in contact with a pulmonary vein and/or the atrial surface, in order to form a lesion by radiant energy. The projected energy can be electromagnetic radiation (e.g., visible light, infrared, ultraviolet or microwave) or ultrasound. The energy can be focused by either refractive or reflective elements. This contact-sensing feature can be implemented by an illumination source and an endoscope situated within the instrument. The image captured by the endoscope from the reflected light can be used to determine whether contact has been achieved and whether such contact is continuous over a desired ablation path. The image data can further be used to confirm lesion formation and/or determine the extent of the spot lesions. The image data can also be enhanced by selective wavelength capture, optical filtering, or other image data processing techniques.

Monitoring allows the clinician to observe balloon inflation and establish an optimal size (with sufficient contact for ablation). Reflective monitoring and/or imaging, especially with wide field of view optics, can be used to determine if the instrument is too deep within a pulmonary vein by mapping tissue contact on the balloon. For example, tissue contact with proximal (rear) portions of the balloon can indicate over-insertion of the balloon in to a vein. Because the device has a wide angle field of view and a large depth of field the clinician can also see the relationship of the balloon to the pulmonary vein ostia. This capability allows the clinician to determine if the balloon is too deep in the pulmonary vein because the optical sensor has the ability to see a large portion of the interior the balloon. For example, if a large extent of tissue contact is observed (or otherwise sensed) proximal to the equator of the balloon (the circumferential zone of greatest diameter), this can indicate that the instrument is too deep in the vein and the creation of lesions in this configuration may pose a risk of causing pulmonary vein stenosis.

In addition, because inflation of the compliant balloon can be observed under direct visualization, the clinician can determine if the balloon is stretching the vein radially by assessing if full contact is achieved before the balloon is completely inflated. This stretching condition would also indicate that the balloon is too distal in the pulmonary vein and could cause damage.

When used in conjunction with a radiant energy emitter, the endoscope and ablation element can be introduced as an assembly. In such configurations, the energy emitter can also serve as the illumination source by operating at a low power level to provide the light for image acquisition. In some embodiments, either the endoscope or the ablative element (or both) can be independently positionable within the instrument.

In addition to determining the degree of contact between the instrument and the tissue, the endoscope can be used to determine the extent of tissue ablation by sensing the change in color of the tissue as it is ablated. Moreover, the endoscope can be used to detect the formation of potentially dangerous coagulated blood at the site of ablation and to allow the clinician to terminate the ablation if necessary for safety reasons. The endoscopic image can also be used to extract colorimetric data, e.g., to distinguish between tissue and blood.

In a further embodiment of the invention, the compliant balloon is expandable to fill the space between the energy emitter and the target tissue with an energy-transmissive fluid and, thereby, provide a transmission pathway for projected radiant energy. The balloon can further be used to collapse trabecular tissue. The instrument can further include a radiant energy delivery element movable within the lumen of the catheter body such that it can be disposed at the desired location and deliver radiant energy through a transmissive region of the instrument to a target tissue site. The movable energy emitter thus permits multi-step treatments, e.g., encircling an asymmetric vein structure with a series of arc-shaped lesions, without the need for repositioning of the balloon or any other portion of the instrument. The instrument can further include additional elements, such fluid delivery ports, to provide a blood-free transmission pathway from the energy emitter to the tissue target. In accordance with the invention, an endoscope is disposed within the projection balloon to monitor and/or guide instrument placement.

In other embodiments, a non-elastic or partially non-elastic balloon can be useful in compressing or collapsing tissue to define a focal region into which a uniform dose of ablative energy can be projected or reflected. More generally, such balloon structures can be used to smooth irregular tissue surfaces and/or define focal planes or curved focal surfaces for the delivery of ablative energy to cardiac tissue in contact with such surfaces.

The use of radiant energy, in conjunction with balloon catheter structures of the present invention that are substantially transparent to such radiation at the therapeutic wavelengths, is particularly advantageous in affording greater freedom in selecting the location of the lesion, e.g., the site is no longer limited to the pulmonary vein itself. Because the energy can be projected onto the tissue in a series of overlapping spots, a ring-like lesion can be formed in atrial tissue at a distance from the vein, thereby reducing the potential for stenosis and/or other damage to the vein itself. Endoscopic-guidance allows the clinician to select a desired lesion location and implement a desired ablation plan by appropriate placement of the radiant energy emitter.

In certain embodiments, infrared radiation is particularly useful in forming photoablative lesions. In certain preferred embodiments, the instruments emit radiation at a wavelength in a range from about 800 nm to about 1100 nm, and preferably emit at a wavelength in a range of about 960 nm to about 1000 nm or in a range of about 1030 nm to about 1090 nm.

Radiation at a wavelength of 960 nm, 980 nm or 1000 nm is commonly preferred, in some applications, because of the optimal absorption of infrared radiation by cardiac tissue at these wavelengths. Such infrared radiation can also be useful as illumination light for the endoscope when provided at a sufficiently low power to capture images without untoward damage to the image capture elements of the invention. Alternatively, ablation can be performed with infrared radiation while one or more white light sources can serve as the illumination component.

In another embodiment, focused ultrasound energy can be used to ablate cardiac tissue. In certain preferred embodiments, an ultrasound transducer can be employed to transmit frequencies within the range of about 5 to about 20 MHz, and preferably in some applications within the range of about 7 MHz to about 10 MHz. In addition, the ultrasonic emitter can include focusing and/or reflective elements to shape the emitted energy into an annular beam or other desired shape.

However, in certain applications, other forms of radiant energy can also be useful including, but not limited to, other wavelengths of light, other frequencies of ultrasound, x-rays, gamma-rays, microwave radiation and hypersound.

In the case of radiant light, the energy delivering element can include a light transmitting optical fiber adapted to receive ablative radiation from a radiation source and a light emitting tip at a distal end of the fiber for emitting radiation. The light delivering element can be slidably and rotatably disposed within an inner lumen of the catheter body and the instrument can further include translatory and rotational mechanisms for disposing the tip of the light delivering element at one or more of a plurality of locations with the catheter.

The present invention provides mechanisms for visualizing where the energy will be applied prior to treatment. In one embodiment, the energy delivering element can include an aiming light source to project visible light onto the tissue, and reflected light can be observed via the endoscope. This visible light from the aiming beam provides an indication to the clinician of the exact location of energy delivery. Markers on the balloon are also disclosed for such visualization based on known correlations between the variable position of the energy source and particular regions of the balloon. In another embodiment, virtual markers are employed. Based on such visual data, the location of ablation element can be selected to optimize the lesion formed upon activation of the ablation element.

In certain preferred embodiments the balloon is filled with a radiation-transmissive fluid so that radiant energy from the energy emitter can be efficiently passed through the instrument to the target region. The fluid can also be used to cool the energy emitter through conduction or via a closed or open circulator system. In certain applications, it can be desirable to use deuterium oxide (so-called "heavy water") as a balloon-filling fluid medium because of its loss absorption characteristics vis-à-vis infrared radiation. In other applications, the inflation fluid can be water or saline or an admixture of such fluids with deuterium oxide (to enhance ablative energy transmission) and/or sodium diatrazoate (to enhance radiographic imaging). The inflation fluid can also be circulated, e.g., via a pump in a base station, to maintain the balloon in an inflated state while also extracting heat. In certain preferred embodiments the balloon is formed at least partially of an elastic material such as polyurethane.

In some applications, it can also be desirable to employ an irrigation or ablative fluid outside of the instrument (e.g., between the balloon and the target region) to ensure efficient transmission of the radiant energy when the instrument is deployed. An "ablative fluid" in this context is any fluid that can serve as a transmitter or conductor of the radiant energy. This fluid can be a physiologically compatible fluid, such as saline, or any other non-toxic aqueous fluid that is substantially transparent to the radiation. In one preferred embodiment, the fluid is released via one or more exit ports at or near the distal tip of the catheter and flows between the balloon and the surrounding tissue, thereby filling any gaps where the balloon does not contact the tissue. The fluid can also serve an irrigation function by displacing any blood within the path of the radiant energy, which could otherwise interfere because of the highly absorptive nature of blood with respect to radiant energy at certain wavelengths.

Similarly, if the radiant energy is acoustic, aqueous coupling fluids can be used to ensure high transmission of the energy to the tissue (and likewise displace blood that might interfere with the radiant acoustic energy transfer).

The ablative or irrigation fluids of the present invention can also include various other adjuvants, including, for example, photosensitizing agents and/or pharmacological agents.

In another aspect of the invention, methods are disclosed for selecting a site for cardiac tissue ablation by positioning a guide wire in a portion of the heart; passing a deflectable sheath catheter over the guide wire such that it can be disposed in proximity to a pulmonary vein; delivering an ablation catheter through the lumen of the deflectable sheath catheter to the vicinity of the vein; inflating the compliant balloon at the ostium of the vein and disposing the spot-generating energy emitter at a position suitable to begin the formation of a series of overlapping lesions. The method can further include continuing formation of overlapping lesions until a circumferential portion of the atrium surrounding the pulmonary vein has been ablated, and then repeating the procedure at one or more additional pulmonary veins. The method can further include determining whether the compliant balloon is located in a desired location and/or whether lesions are properly formed based on images captured by the endoscope.

BRIEF DESCRIPTION OF THE DRAWINGS

The invention will be more fully understood from the following detailed description taken in conjunction with the accompanying drawings, in which like reference numerals designate like parts throughout the figures, and wherein:

FIG. 15 is a schematic cross-sectional view of an endoscope useful in the present invention FIG. 16 is a schematic illustration of a translation system for independently positioning the endoscope and ablation components of an endoscope/ablator assembly during a procedure;

FIG. 17 is a side perspective view of a translatory mechanism for controlled movement of a radiant energy emitter within the instruments of the present invention.

DETAILED DESCRIPTION

Figure 1:
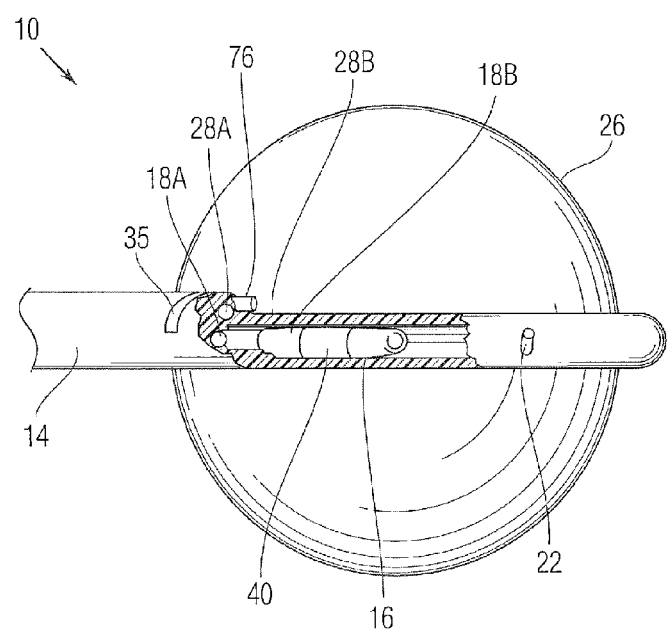
FIG. 1 is a schematic, partially-cutaway view of a cardiac ablation instrument according to the invention.

FIG. 1 provides a schematic, cross-sectional view of an ablation instrument 10 according to the invention, including an elongate body 14, a central lumen tubing 16 and a compliant balloon 26 inflatable via one or more ports 22 in the central tubing. The central tubing 16 can also house an energy emitter that is capable of both axial movement and rotation within the tubing 12. Within the elongated body (also referred to herein as the catheter body) there can be a plurality of additional lumens, through which certain devices or instruments can been passed. For example, as shown in FIG. 1, the catheter body 14 also provides lumens 18A and 18B for extraction (or circulation) of a inflation fluid, an endoscope 76 and illuminations fibers 28A and 28B. The catheter body can carry a marker to assist the clinician in proper placement of the device, e.g., a radiopaque marker to aid in fluoroscopic detection.

Figure 2A:
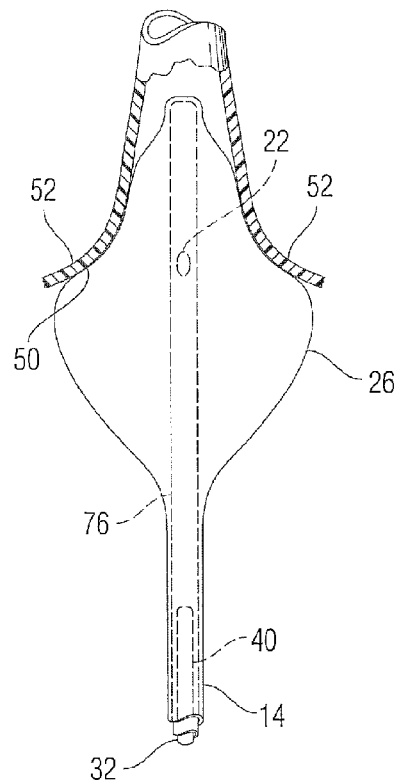
FIG. 2A is a schematic view of the cardiac ablation instrument of FIG. 1 in a treatment position at the ostium of pulmonary vein.
Figure 2B:
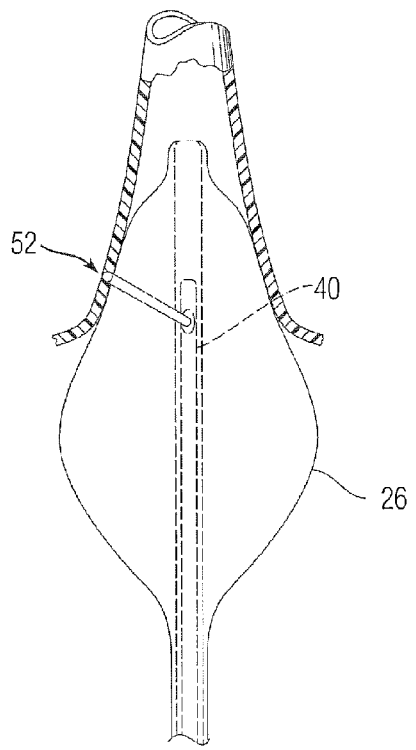
FIG. 2B is a schematic view of the cardiac ablation instrument of FIG. 1 with its compliant balloon inflated and its ablation element deployed at one of a plurality of locations.

As shown in FIG. 2A, the instrument is preferably designed such that upon disposition within the heart (e.g., proximal to a pulmonary vein), the balloon can be inflated such that a shoulder portion 50 of the balloon 26 will be urged into close proximity with a target region 52 of cardiac tissue (e.g. an region of the atrial heart wall surrounding the ostium of a pulmonary vein). As shown in FIG. 2B. the energy emitter (or "lesion generator") 40 can be positioned to delivery ablative energy 21 to the target region 52 to form a lesion.

It should be understood that the embodiments illustrated in the drawings are only a few of the cardiac ablation instruments that can utilized the present invention. Further descriptions of other embodiments can be found, for example, in commonly owned, co-pending U.S. patent application Ser. No. 10/357,156, filed Feb. 3, 2003 and U.S. patent application Ser. No. 09/924,393, filed Aug. 7, 2001, both of which are expressly incorporated by reference.

The instrument can optionally include one or more ports for delivering irrigation fluid to the target region. When the device employs radiant energy ablation, the fluid is preferably an energy transmissive medium, which helps deliver light, radiation or acoustic energy from a radiant energy source to a target tissue region. The fluid also serves to clear blood from the vicinity of the instrument and compensate for irregularities in the shape of the heart that might otherwise compromise the seating of the instrument. The ablative fluid thus provides a clear transmission pathway external to the balloon.

Returning to FIG. 2B, a radiant energy emitter 40 is shown disposed within the projection balloon 26 remotely from the target tissue (e.g., within a central lumen of the catheter body 14 or otherwise disposed within the balloon). In one embodiment, the radiant energy source includes at least one optical fiber coupled to a distal light projecting, optical element, which cooperate to project a spot of ablative light energy through the instrument to the target site. The catheter body, projection balloon and inflation/ablation fluids are all preferably substantially transparent to the radiant energy at the selected wavelength to provide a low-loss transmission pathway from the ablation element 40 to the target.

Also disposed within the instrument is a reflectance sensor, preferably an endoscope 76 capable of capturing an image of the target site and/or the instrument position. The endoscope is typically an optical fiber bundle with a lens or other optical coupler at its distal end to receive light. The reflectance sensor/endoscope can also include an illumination source, such one or more optical fibers coupled to a light source or sources. Endoscopes are available commercially from various sources. The endoscope can further include an optical head assembly, as detailed in more detail below, to increase the field of view. In one preferable embodiment, ablation element 40 and endoscope 76 are adapted for independent axial movement within the catheter body 14.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of a object to a location for viewing. The viewing location can be direct, e.g., an eyepiece, or indirect, e.g., an image capture device, such as a CCD camera, which converts image data into a video display.

In certain preferred embodiments, the balloon is a compliant balloon, e.g. an elastic balloon which is expandable to a variable volume to accommodate pulmonary veins (or other target sites of various sizes, thereby alleviating the need to deploy a balloon catheter instrument based on an estimated or assumed vein size and then remove and redeploy another instrument if the cardiac anatomy is different than predicted at the outset.

Figure 3:
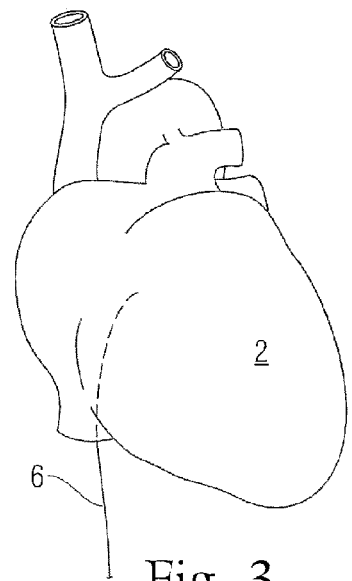
FIG. 3 is a schematic illustration of an initial step in performing ablative surgery according to the invention, in which a guide wire is percutaneously inserted into the heart.
Figure 4:
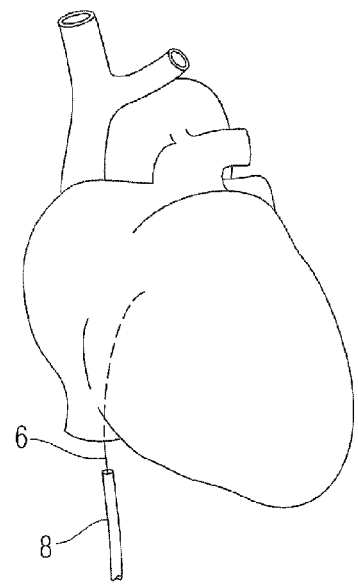
FIG. 4 is a schematic illustration of a further step in performing ablative surgery in which a deflectable sheath catheter is deployed in the heart over the guide wire.
Figure 5:
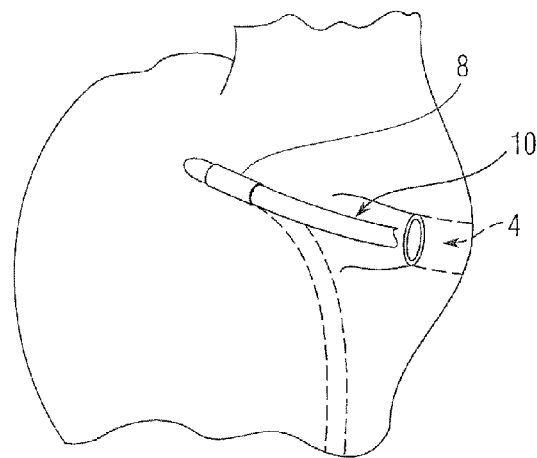
FIG. 5 is a schematic illustration of a further step in performing ablative surgery in which a deflectable sheath catheter is maneuvered into a position proximal to a pulmonary vein and the guide wire is withdrawn and replaced with an ablation catheter according to the invention.
Figure 6:
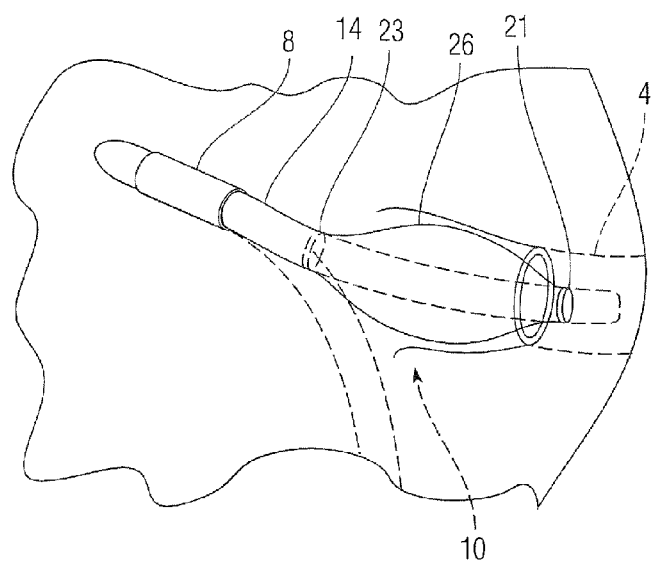
FIG. 6 is a schematic illustration of a further step in performing ablative surgery in which a balloon structure of the present invention is inflated at the ostium of a pulmonary vein.

FIG. 3 is a schematic illustration of an initial step in performing ablative surgery with radiant energy according to the invention, in which a guide wire 6 is introduced into a heart 2 and passed into the left atrium. FIG. 4 is a schematic illustration of a method of performing ablative surgery with radiant energy according to the invention. After guide wire 6 is be introduced into a heart 2 and passed into the atrium, a deflectable sheath catheter 8 is slid over the guide wire 6. The sheath catheter can be advanced, for example, into the left atrium of the heart. The guide wire can then be withdrawn and replaced with a percutaneous ablation instrument 10 according to the invention as shown schematically in FIG. 5. The catheter 10 then be advanced to a position proximal to the ostium or mouth of a pulmonary vein, as shown in FIG. 6, where its balloon element can be inflated. For this purpose, the catheter 10 can further include at least one internal fluid passageway (not shown) for inflation of the balloon 26, which is sealed to the body of the catheter 10 by distal seal 21 and proximal seal 22, such that the introduction of an inflation fluid into the balloon 26 can inflate the balloon.

With reference again to FIG. 2B, the balloon 26 is inflated to define a projection pathway for radiant energy ablation of cardiac tissue. The expanded balloon defines a staging through which radiant energy can be projected in accordance with the invention. In one preferred embodiment, the projection balloon is filled with a radiation-transmissive fluid, such as deuterium oxide (so-called "heavy water") so that radiant energy from an energy emitter can be efficiently passed through the instrument to a target region 52 of cardiac tissue.

In another aspect of the invention, spot lesions are formed by applying radiant energy to target tissue in a range from about 50 Joules/cm$^2$ to about 1000 Joules/cm$^2$, or preferably from about 75 Joules/cm$^2$ to about 750 Joules/cm$^2$ In certain embodiments, the power levels applied by the energy emitter can range from about 10 Watts/cm$^2$ to about 150 Watts/cm$^2$ and the duration of energy delivery can range from about 1 second to about 1 minute, preferably from about 5 seconds to about 45 seconds, or more preferably from about 10 to about 30 seconds. For example, for power levels between 10 and 75 Watts/cm$^2$ it can be advantageous to apply the radiant energy for about 30 seconds. Lesser durations, e.g., of 10 to 20 seconds, can be used for power levels of 75 to 150 Watts/cm$^2$.

The balloons described herein can be preshaped to form parabolic like or various other shapes (e.g., to assist in seating the instrument at the mouth of a pulmonary vein or otherwise engaging the vein ostium or other anatomically defined regions of the heart). This can be accomplished, for example, by shaping and melting a polymeric film in a preshaped mold to effect the desired form. Compliant balloons according to the present invention can be made, for example, of thin wall polyurethane with a membrane thickness of about 5-50 micrometers, and, in some applications, preferably less than 10 micrometers or less than 5 micrometers in thickness in an inflated state. The balloon is also preferably an elastic or pliable material, e.g., with a durometer ranging from about 35A to about 55D, or preferably from about 75A to about 95A, as measured according to the Shore durometer scales.

It should be noted that it is not necessary for the balloon 26 to contact the target tissue in order to ensure radiant energy transmission. One purpose of the projection balloon is simply to clear a volume of blood away from the path of the energy emitter. With reference again to FIG. 2B, an ablative fluid can be employed outside of the instrument (e.g., between the balloon 26 and the target region 52) via irrigation ports (not shown) to ensure efficient transmission of the radiant energy when the instrument is deployed. The ablative fluid in this context is any fluid that can serve as a conductor of the radiant energy. This ablative fluid can be a physiologically compatible fluid, such as saline, or any other non-toxic aqueous fluid that is substantially transparent to the radiation. The fluid can also serve an irrigation function by displacing any blood within the path of the radiant energy, which could otherwise interfere with the radiant light energy transmission to the target region 52.

For alternative designs for delivery of ablative and/or irrigation fluids, see commonly-owned, U.S. patent application Ser. No. 09/660,601, filed Sep. 13, 2000 entitled "Balloon Catheter with Irrigation Sheath," the disclosures of which are hereby incorporated by reference. For example, in one embodiment described in patent application Ser. No. 09/660, 601, the projection balloon can be partially surrounded by a sheath that contains pores for releasing fluid near or at the target ablation site. One of ordinary skill in the art will readily appreciate that such pores can vary in shape and/or size. A person having ordinary skill in the art will readily appreciate that the size, quantity, and placement of the fluid ports of various designs can be varied to provide a desired amount of fluid to the treatment site.

In one illustrated embodiment, shown in more detail below, the energy emitter 40 can be a radiant energy emitter and includes at least one optical fiber 42 coupled to a distal light projecting, optical element 43, which cooperate to project a spot of ablative light energy through the instrument to the target site. The optical element can further comprise one or more lens elements and/or refractive elements capable of projecting a spot or arc-shaped beam of radiation. Alternatively, the lesion generator may generate a annulus or partial ring of ablative radiation, as described in more detail in commonly owned U.S. Pat. No. 6,423,055 issued Jul. 22, 2002, herein incorporated by reference.

In one preferred embodiment, the optical element is adapted to project an arc-like pattern of radiation and the energy emitter can be rotated and/or translated to encircle the pulmonary vein. Alternatively, the radiant energy emitter can be an ultrasound or microwave energy source, as described in more detail below that is likewise configured to generate a series of vein-encircling spot lesions.

Figures 7, 8:
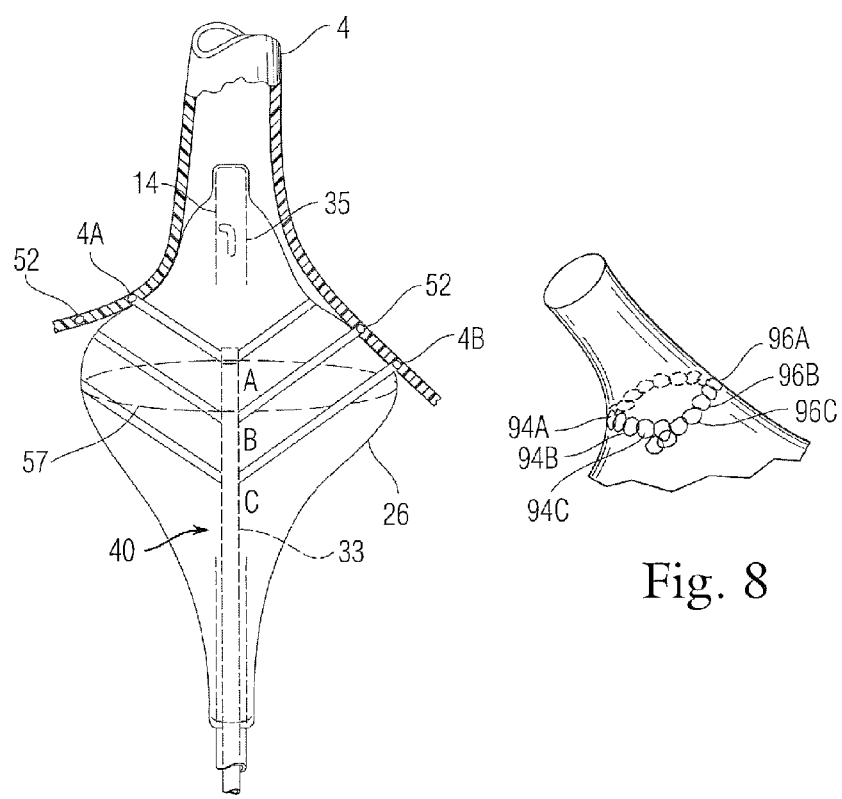
FIG. 7 is a schematic view of the cardiac ablation instrument with its compliant balloon inflated and illustrating how its ablation element can be deployed at different locations to direct radiant energy through different regions of the balloon when an asymmetric vein mouth is encountered and further showing how the position of the radiant energy emitter can be adjusted to select a desired location.
FIG. 8 illustrates how a continuous, vein-encircling lesion can be formed by a series of overlapping spot lesions.

FIGS. 7 and 8, taken together, also illustrate an advantageous feature of the present invention, namely, the ability to select the location of a lesion independent of the instrument design or location. Because the radiant energy emitter does not require contact with a target tissue region and is, in fact, decoupled from the rest of the instrument, the present invention permits the clinician to select a desired target region by simply moving the emitter (e.g., within the lumen of the catheter). As shown in FIG. 7, the radiant energy emitter can be positioned to form a wide circumferential lesion (when the shape of the pulmonary vein ostium warrants such a lesion) by positioning the radiant energy emitter at the rear of the projection balloon—at a distance from the target tissue denoted as "C". Alternatively, a smaller diameter lesion can be formed by positioning the radiant energy emitter closer to the front of the projection balloon, as shown in positions "A" or "B". Smaller lesions can be preferable when the geometry of the vein ostium presents a sharper change in diameter, as shown by schematic wall segment 4B. It should be appreciated that it may be desirable to change the intensity of the emitted radiation depending upon the distance it must be projected; thus a more intense radiant energy beam may be desirable in the scheme illustrated in position "C" in comparison with position "A.".

In addition, the expandable element can include one or more orientation markers 57 that can be visualized endoscopically, to aid in determining the location of tissue contact or targeted energy delivery relative to geometric features of the expandable element. For example, the orientation marker 57 may take the form of an endoscopically visible circumferential line on the portion of the expandable element that generally presents the largest diameter upon inflation. In the endoscopic view this line appears as circle. This circles acts as an aide in determining the optimal amount of energy to deliver to a given portion of tissue when the tissue is viewed endoscopically. When energy is delivered substantially near the circle as seen in the endoscopic view the operator will select a larger amount energy since energy delivery near the circle is know to be energy delivery substantially near the maximum diameter of the expandable element. If energy is delivered substantially outside of or substantially inside of the circle the user will know to deliver a lower amount of energy since such deliveries are substantially near the smaller diameter proximal and distal portions of the expandable element respectively. In a similar manner the expandable element may contain a series of circumferential lines corresponding to generally differing diameters and appearing as generally concentric circles in the endoscopic view each circle being associated with an amount of energy generally corresponding to the associated diameter of the expandable element. These concentric circles may also be radiopaque and visible fluoroscopically as a further aid to understanding the geometric relationship of the balloon to the complex left atrial anatomy.

The energy emitter 40 and catheter body 14 can each include one or more markers (shown schematically as elements 33 and 35 respectively) to aid in determining the location or tracking movements of the elements. Markers 33 and 35, for example, can be radiopaque lines that can visualized fluoroscopically.

In addition, the expandable element or the catheter body can include an orientation marker 35 which can be visualized both fluoroscopically and endoscopically or alternatively the catheter body or expandable element may include an orientation marker that can be visualized fluoroscopically and whose location relative to a characteristic feature of the device which can be seen endoscopically is known. These markers are used to visualize the position and/or rotational orientations of the catheter body relative to the patients anatomy. Each of the markers 35 can be suitably shaped to provide rotational information when viewed fluoroscopically. For example, the markers can be shaped in the form of an "L" to assist in understanding the rotational orientation. Once the rotational orientation of the catheter body is know the endoscopic view may be rotated either by electronically manipulating the video image or by rotating the endoscope fiber relative to the video camera. The goal of rotating the image is to achieve an orientation such the user may understand where on the endoscopic image the superior, posterior, inferior etc. aspect of the pulmonary vein is located. This information is important for two reasons. First two anatomical structures to be avoided during pulmonary vein ablation are the phrenic nerve and the esophagus. Both these structures are located near the posterior portion of the left atrium. Generally lower amounts of energy are preferred to be used when ablating the posterior regions of the veins. Alternatively scrupulous attention to output temperature probes typically placed in the lumen of the esophagus is paid when ablating the posterior aspect of pulmonary veins. Secondly the anterior aspect of some pulmonary veins such as the right superior pulmonary vein are know to generally be thicker than other parts of the veins an consequently a higher energy dose is desired in these regions. Various other marker mechanisms, such as magnetic, capacitive or optical markers, can also be used. The deflectable sheath used to introduce the catheter can be similarly marked to assist in fluoroscopic observation.

If the catheter itself is constructed of a low modulus material, it may be desirable to reinforce it to make more rotationally stable. For example, the catheter can be reinforced by one or more longitudinal rib elements or a braid layer so that it can be more easily "torqued" to overcome endoscopic blind spots or other achieve a desired orientation.

Typically with prior art devices, the target site, e.g., the ostium of a pulmonary vein, can only be located by fluoroscopic inspection during injection of a contrast medium into the vein. Such images are transient. Location of the ablation catheter itself, even with radiopaque markers, is likewise difficult because of the geometry of the heart. Moreover the heart's structure is largely invisible during fluoroscopic inspection.

Endoscopic guidance systems coupled with the use of orientation markers can help overcome these problems. The use of radiopaque markers on the endoscope and/or the catheter allow the user to orient the ablation instrument relative to the pulmonary vein and permit anatomical features seen via the endoscope to be combined with fluoroscopic information. Orientation markers, such as elements 33 and 35 can be used to determine the angular position of the instrument relative to structures such the ostia and also provide a measure of how far a movable element, such as the energy emitter 40, has been advanced within the instrument. (It should be appreciated that numerous other marker schemes can be employed to achieve these objectives, including ring markers on either the energy emitter and/or the catheter body.)

Similarly, the ring marker shown as element 57 on the projection balloon 26 can be replaced by a series of rings. Alternatively, if the endoscope is maintained in a fixed position relative to the balloon, physical markers can be replaced with virtual markers generated electronically as part of the display. Such information is particularly useful in selection one or more of alternative sites for ablation. In addition to the movable energy emitters described herein, the invention can be used in conjunction with two or more fixed ablation elements (e.g., resistive heating bands of different circumferences) to select the most appropriate one (or set) of the ablation elements to be activated for lesion formation.

The endoscopic guidance systems of the present invention can further be used to position any movable point source of ablative energy, e.g., a rotating contact or radiant ablation element in lieu of a slidably positionable source or together therewith, such that the desired path for circumferential can be visualized and followed by the ablation element. Most generally, the endoscopic guidance systems of the invention can be used together with various fluoroscopic or other imaging techniques to locate and position any one of the various instruments necessary for cardiac ablation.

The ability to position the energy emitter, especially when radiant light is employed as the ablation modality, also permits endoscopic aiming of the energy. For example, an aiming light beam can be transmitted via the catheter to the target site such that the physician can visualize where the energy will be delivered. Thus, endoscopic guidance permits the user to see where energy will be projected at various locations of the energy emitter. Thus, if the instrument is designed to project light in an annular ring (or arc or spot) around the ostium of a pulmonary vein, the aiming beam can be projected down the same optical delivery path as would the radiant energy. If the "aiming beam" is projected onto a region of the atrium where a clear transmission pathway is seen (e.g., there is continuous contact (or the desired lesion path is otherwise cleared of blood), then the physician can begun the procedure. If, on the other hand, a clear transmission pathway is not seen at a particular location of the ablation element, then the ablation element can be moved until a clear lesion pathway is found.

Although this "aiming" feature of the invention has been described in connection with radiant light energy sources, it should be clear that "aiming" can be used advantageously with any radiant energy source and, in fact, it can also assist in the placement of fixed or contact-based ablation elements. Most generally, endoscope-guidance can be combined with an aiming beam in any cardiac ablation system to improve positioning and predetermination of successful lesion formation.

The terms "visual," "visualize," "observe" and derivatives thereof are used herein to describe both human and machine uses of reflectance data. Such data can take the form of images visible to a clinician's eye or any machine display of reflected light, e.g., in black & white, color or so-called "false color" or color enhanced views. Detection and display of reflected energy measurements outside the visible spectrum are also encompassed. In automated systems such visual data need not be displayed but rather can be employed directly by a controller to guide the ablation procedure.

FIG. 7-8 further illustrates the unique utility of the multi-positionable, radiant energy ablation devices of the present invention in treating the complex cardiac geometries that are often encountered. As shown in the figure, the mouths of pulmonary veins typically do not present simple, funnel-shaped, or regular conical surfaces. Instead, one side of the ostium 4B can present a gentle sloping surface, while another side 4A presents a sharper bend. With prior art, contact-heating, ablation devices, such geometries will result in incomplete lesions if the heating element (typically a resisting heating band on the surface of an expandable element) can not fully engage the tissue of the vein or ostium. Because the position of the heating band of the prior art devices is fixed, when it does not fully contact the target tissue, the result is an incompletely formed, partially circumferential, lesion that typically will be insufficient to block conduction.

FIG. 7 illustrates how the slidably positionable energy emitters of the present invention can be used to avoid this problem. Three potential positions of the emitter 40 are shown in the figure (labeled as "A", "B" and "C"). As shown, positions A and C may not result in optimal lesions because of gaps between the balloon and the target tissue. Position B, on the other hand, is preferable because circumferential contact has been achieved. Thus, the independent positioning of the energy source relative to the balloon allows the clinician to "dial" an appropriately ring size to meet the encountered geometry. (Although three discrete locations are shown in FIG. 4, it should be clear that emitter can be positioned in many more positions and that the location can be varied in either discrete intervals or continuously, if so desired.)

Figure 14A:
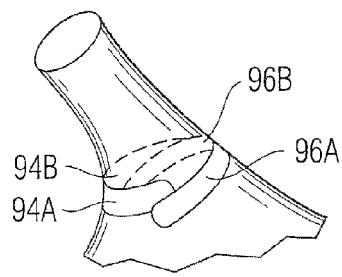
FIG. 14 is a schematic illustration of an alternative embodiment of a radiant energy emitter according to the invention employing ultrasound energy.
Figure 14B:
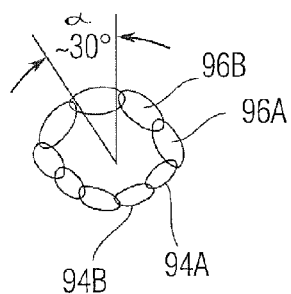

Moreover, the geometries of the pulmonary veins (or the orientation of the projection balloon relative to the ostia) may be such that no single annular lesion can form a continuous conduction block. Again, the present invention provides a mechanism for addressing this problem by rotation and adjustment of the location of the energy emitter to form a series of spot lesions that overlap and create a circumferential block. As shown in FIGS. 14A and 14B, the devices of the present invention can form a first series of lesions 94A, 94B, 94C, etc. by rotation along a first arc when the energy emitter is in a first location and a second series of lesions 96A, 96B, 96C, etc. by rotation along a second arc when the energy emitter is in a second location. Because each spot lesion has an area (dependent largely by the amount of energy deposited into the tissue) the spot lesions can combine, as shown, to form a continuous encircling or circumscribing lesion that blocks fibrillation-inducing electric conduction. Although illustrated as two series of spot lesions along two curved paths, it should be clear that any number of paths (emitter locations) can be chosen in order to complete vein isolation. Moreover, the size of the spots can be varied, e.g., by depositing more energy in a particular location, in the course of a procedure.

Figure 9:
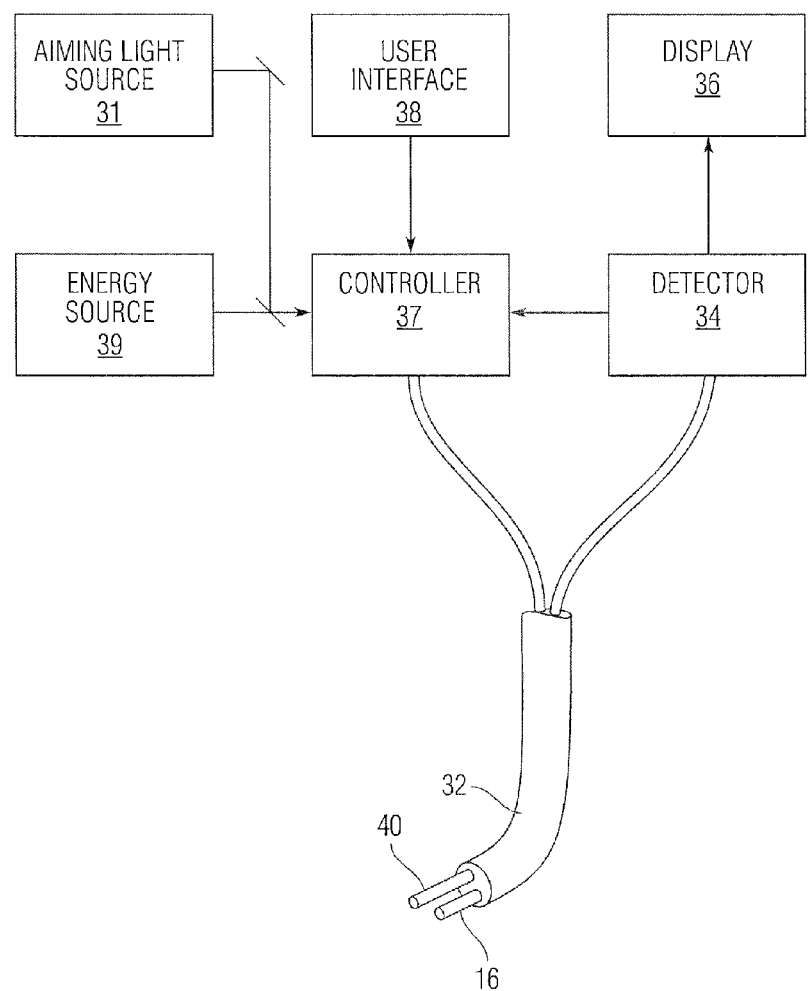
FIG. 9 is a schematic block diagram of the components of an endoscope-guided cardiac ablation system according to the invention.

FIG. 9 is a schematic block diagram shown the endoscope/ablator assembly 32 comprising endoscope 76 and ablation element 40 connected to an analyzer system. The analyzer system further includes a detector 34 for detecting reflected light (and preferable for generating a image). The output of the detector 34 can be transmitted to a display 36 for clinician viewing. The display 36 can be a simple eyepiece, a monitor or a heads-up projection onto glasses worn by members of the surgical team. The system can further include an energy source 39, a controller 37 and a user interface 38. In use, the endoscope 76 captures images which can be processed by the detector 34 and/or controller 37 to determine whether a suitable ablation path can be created. An aiming light source 31 can also be used visualize the location where energy will be delivery to the tissue. If a suitable ablation path is seen by the surgeon, the controller 37 can transmit radiant energy from the ablation element 39 to a target tissue site to effect ablation. The controller can further provide simulated displays to the user, superimposing, for example, a predicted lesion pattern on the image acquired by the detector or superimposing dosimetry information based on the lesion location. The controller can further include a memory for storing and displaying data, such as pre-procedure images, lesion predictions and/or actual outcomes. The controller can further provide a safety shutoff to the system in the event that a clear transmission pathway between the radiant energy source and the target tissue is lost during energy delivery.

Figure 10:
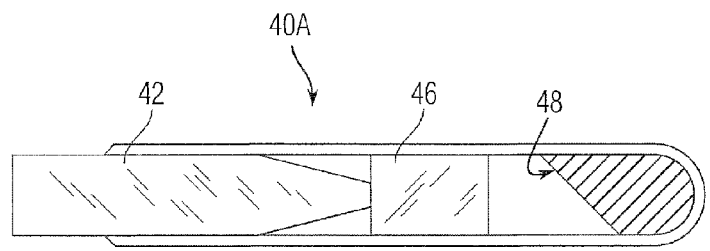
FIG. 10 is a schematic illustration of one embodiment of a radiant light energy emitter according to the invention.
Figure 11:
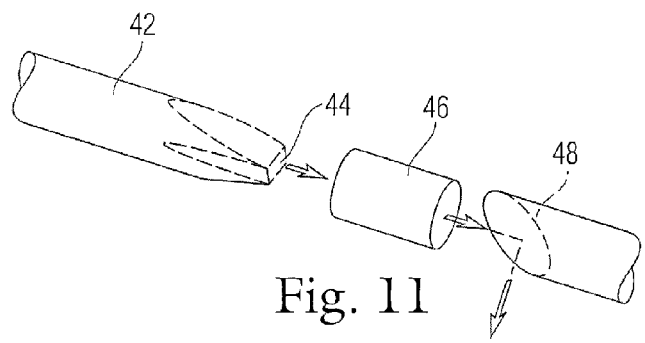
FIG. 11 is a schematic exploded view of the optical elements of the emitter of FIG. 10.

FIG. 10 is a schematic cross-sectional illustration of one embodiment of a radiant energy emitter 40A according to the invention. FIG. 11 is a schematic perspective view of the principal optical components of the emitter. In one preferred embodiment, the radiant energy is electromagnetic radiation, e.g., coherent or laser light, and the energy emitter 40A projects an beam of radiation that forms a spot or arc-shaped exposure pattern upon impingement with a target surface. For example, radiant energy emitter 40A can include an optical fiber 42, the distal end of which is beveled into an energy-emitting face 44 of reduced cross-section. the fiber 42 passes an beam of light to a gradient index (GRIN) lens 46, which serves to collimate the beam, keeping the beam width the substantially the same, over the projected distance. The beam that exits the GRIN lens is reflected by reflector 48 in an angular direction from about 5 degrees to about 110 degrees relative to from the light's path along the longitudinal axis of the catheter. Generally, the angle of reflection from the central axis of the optical fiber 42 can range from about 30 to nearly 90 degrees. In other words, the angle of projection, from the optical axis of the fiber 42 (or lens 46) will be between about 5 to 60 degrees forward of perpendicular.

Figure 12:
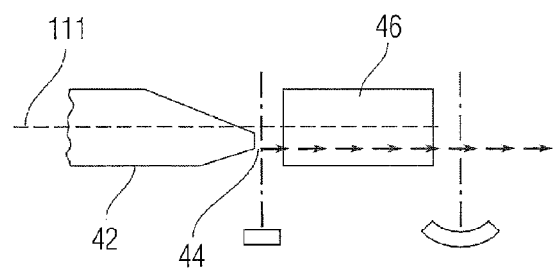
FIG. 12 is a schematic illustration of another embodiment of a radiant light energy emitter according to the invention in which the elements are configured to project a arc-shaped spot of ablative energy.

FIG. 12 is a schematic illustration of a variant on the optical assembly of FIGS. 10 and 11, in which the beveled distal end 44 of the fiber 42 is offset from the centerline 111 of the longitudinal axis, causing light propagating through the GRIN lens 46 to be bent into an arc-shaped exposure pattern. Overlapping patterns of such arc-shaped spots can be used advantageously to form an encircling lesion. The subtended angle of projected annular light, a, can be between about 20 and about 60 degrees, preferably between about 25 and about 35 degrees, most preferably in some applications about 30 degrees.

Figure 13:
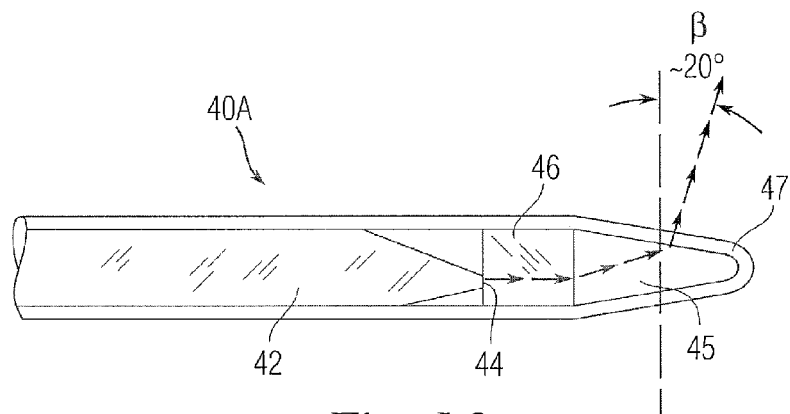
FIG. 13 is a schematic illustration of another embodiment of a radiant light energy emitter according to the invention.

FIG. 13 is a schematic illustration of another embodiment of a radiant energy emitter 40A according to the invention.

Again, in this embodiment, the radiant energy is electromagnetic radiation, e.g., coherent or laser light, and the energy emitter 40A projects a beam of radiation that forms a spot or arc-shaped exposure pattern upon impingement with a target surface. For example, radiant energy emitter 40A can include an optical fiber 42 again having a beveled distal tip offset from the central axis. Ablative energy entering the gradient index (GRIN) lens 46 will be formed into an arc-shaped beam of light. The GRIN lens 46 also serves to collimate the beam, keeping the beam width the same, over the projected distance. The beam that exits from the GRIN lens 46 will be refracted first in the air gap 45 of the distal end cap and again as it passed through the wall of the end cap. The projected light beam will expand (in diameter) over distance, but the energy will remain largely confined to a narrow annular band. Generally, the angle of projection, β, from the optical axis of the fiber 42 (or lens 46) will be between about 5 to 60 degrees forward of perpendicular. Again, the subtended angle of the arc-shaped spots can be between about 20 to about 60 degrees, preferably between about 25 and about 35 degrees, most preferably in some applications about 30 degrees.

The diameter of the beam of light will be dependent upon the distance from the point of projection to point of capture by a surface, e.g., a tissue site, e.g., an interstitial cavity or lumen. Typically, when the purpose of the radiant energy projection is to form a transmural cardiac lesion, e.g., around a pulmonary vein, the diameter (or minimum width) of the beam will be between about 6 mm and about 20 mm, preferably greater than 10 mm or greater than 15 mm. In some instances a beam width greater than 20 mm can also be useful. The cross-sectional area of the beam at tissue impingement can range from about 5 $mm^2$ to about 500 $mm^2$ to form lesions having average surface areas of the same or similar sizes. In some applications is preferable to control the spot size to create lesions having surface areas of less than about 100 $mm^2$. When the spot is arc-shaped as shown in FIGS. 14A and 14B, the subtended angle of projected annular light is between about 20 and about 60 degrees, preferably between about 25 and about 35 degrees, most preferably in some applications about 30 degrees.

Preferred energy sources for use with the percutaneous ablation instruments of the present invention include laser light in the range between about 200 nanometers and 2.5 micrometers. In particular, wavelengths that correspond to, or are near, water absorption peaks are often preferred. Such wavelengths include those between about 805 nm and about 1070 nm, preferably between about 900 nm and 1100 nm, most preferably, between about 960 nm and 1000 nm. In certain embodiments, wavelengths around 915 nm or around 960 nm around 980 nm can be preferred during endocardial procedures. Suitable lasers include excimer lasers, gas lasers, solid state lasers and laser diodes. One preferred AlGaAs diode array, manufactured by Spectra Physics, Tucson, Ariz., produces a wavelength of 980 nm.

The optical waveguides, as described in above, can be made from materials known in the art such as quartz, fused silica or polymers such as acrylics. Suitable examples of acrylics include acrylates, polyacrylic acid (PAA) and methacrylates, polymethacrylic acid (PMA). Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate.

Internal shaping of the waveguide can be accomplished by removing a portion of material from a unitary body, e.g., a cylinder or rod. Methods known in the art can be utilized to modify waveguide to have tapered inner walls, e.g., by grinding, milling, ablating, etc. In one approach, a hollow polymeric or glass cylinder, e.g., a tube, is heated so that the proximal end collapses and fuses together, forming an integral proximal portion which tapers to the distal end of the waveguide. In another approach, the conical surface 45 can be formed in a solid quartz cylinder or rod by drilling with a tapered bore.

Waveguide 44 can be optical coupled to optical fiber 42 by various methods known in the art. These methods include for example, gluing, or fusing with a torch or carbon dioxide laser. In one embodiment, waveguide 44, optical fiber 42 and, optionally, a gradient index lens (GRIN) 46 are in communication and are held in position by heat shrinking a polymeric jacket material 49, such as polyethylene terephthalate (PET) about the optical apparatus 40.

FIG. 15 illustrates an alternative embodiment of a radiant energy emitter 40C in which an ultrasound transducer 60, comprising individual shaped transducer elements (and/or lenses or reflectors) 62 which direct (project) the ultrasound energy into a spot of energy that can likewise form an annular exposure pattern upon impingement with a target surface. The emitter 40C is supported by a sheath 66 or similar elongate body, enclosing electrical leads, and thereby permitting the clinician to advance the emitter through an inner lumen of the instrument to a desired position for ultrasound emission.

Yet another embodiment of a radiant energy emitter can employ microwave energy similarly focused into a spot or arc-shaped exposure beam. The microwave energy emitter can include a coaxial transmission line (or similar electrical signal leads) and a helical coil antenna. Radiation reflectors can cooperate to shield and direct the radiation into a spot. In other embodiments, a radioisotope or other source of ionizing radiation can be used in lieu of the microwave antenna, again with appropriate radiation shielding elements to project a beam of ionizing radiation.

It should be clear that the invention can be practiced with various numbers of illuminating and/or sensing elements, and with or without use of the energy emitter as an element in the contact sensing module. The emitter and the endoscope can each move independently, if desired. Moreover, ultrasound emitters and detectors can also be used in the same manner in lieu of the light reflecting mechanisms to determine contact. In any event, the output signals of the sensors can be electronically processed and incorporated into a display.

The devices of the present invention can further include illumination elements that are capable of diffusing light to a large contact area of tissue by employing a scattering medium at the distal end of the illumination fiber. Examples of this diffusing material can be a matrix of titanium dioxide particles suspended in cured silicone. This diffusing medium allows high intensity light to be uniformly diffused over a large area preferably over an area greater than 40 mm in diameter.

Endoscopes useful in the present invention can include a coherent optical fiber bundle for transmitting the captured image back to a detector and display. The distal end of the endoscope can be coupled to a set of lenses which create an image at the distal end of the fiber bundle and provide an enhanced field of view. Such field enhancing elements preferably increase the field of view to greater than 50 degrees, more preferably to about 70 degrees or higher. Typically, commercially available endoscopes have a field of view of about 50 degrees or less in air. However, when immersed in water or similar fluids, the field of view of the endoscope is further reduced due to the refractive index difference between water and air. As explained in more detail below, a greater field of view can be very important to endoscopic guidance.

The endoscopes of the present invention provide the ability to position the percutaneous ablation instruments of the present invention at a treatment site such that proper location of the energy emitter vis-à-vis the target tissue (as well a satisfactory degree of contact between the projection balloon and the tissue) is achieved.

FIG. 16 provides a detailed schematic illustration of an endoscope 76A with enhanced field of view. The endoscope can include a fiber bundle 130 within a protective polyimide tube 132 coupled to distal stainless steel tube 134 in which the field-enhancing optics are disposed. Within distal tube 134, an imaging lens 136 and an objective lens 140 are situated, together with a centering and connecting tubes (e.g., tube 135 and 142) as may be needed to secure the lenses in place. (It should be appreciated that various lens combination or compound lens structures can be substituted for the elements shown in FIG. 16.)

The endoscope 76A is designed to have a wide field of view even while it is immersed in liquid. The liquid in which it is immersed typically can be either physiological saline in the inner lumen of the catheter or deuterium oxide which is one preferred medium for filling applicants' projection balloon. Both of these liquids have essentially the same index of refraction. To achieve the wide field of view a lens system such as shown in FIG. A can be used. The lens system consists of two plano-convex lenses 136 and 140 arranged as shown along with an apertured window 144. High index of refraction materials are preferably used for the lenses. Suitable materials include sapphire, cubic zirconia or high index glass materials. Alternatively, air-filled optical structures can be substituted for the solid lenses shown in the figure. All these materials are readily available as small diameter spheres with optical quality surfaces. The spheres can be made into hemispheres and the diameter of the hemispheres are reduced using common lens grinding technology. The aperture can be constructed by metallizing one surface of flat glass plate. The central aperture hole is created by masking the flat glass before the metallization or removing the metallization with a laser.

The ability have a field of view greater that 50 degrees (and, preferably, in some applications, greater than 70 degrees, or 90 degrees) can be important because of the geometry of the heart and the ablation elements. Visualization of the ostium of a pulmonary vein inherently requires a wide field of view. Moreover, the ablation element (including any expandable element) must be short because of the limited space available within the atrial chamber. These two factors combine to require the placement of the endoscope close to the vein and an even wider field of view is desirable, typically greater than 70 degrees, in order to visualize the target region and the instrument's position relative to the target region. Moreover, the wide field of view allows the clinician to see well proximal to the apex of the balloon; thus providing the ability to determine if the instrument is placed too deep in the pulmonary vein.

Thus, formation of ablative lesions for treatment of atrial fibrillations and the like can be accomplished with the instruments and systems described herein by observing balloon location via an endoscope deployed within applicants' catheter devices. For example, the method can include observation of a marker on the balloon to determine orientation of a balloon (or other expandable element) within the heart. The method can further include projecting an aiming beam during (e.g., while or following) positioning of the energy emitter to identify a candidate site for treatment. Preferably, the aiming beam is substantially coaxial with the treatment energy beam and the spot formed by the aiming beam is coincident (e.g., substantially overlaps) with the site to be ablated. In a preferred embodiment, the aiming beam is introduced via a beam combining mirror arrangement (as shown in FIG. 9) such that the aiming beam is projected via the same optical fiber, lens and reflector elements as the treatment beam. The aiming beam can verify that a candidate site is acceptable for ablation by endoscopic observation of where the aiming beam impinges. Any visible wavelength including white light can be used as the aiming beam, however, in certain applications it can be advantageous to employ two or more discrete wavelengths, e.g. red and green light, to visualizing both tissue contact and blood.

Verification can be based on endoscopic observation of balloon contact with tissue in the vicinity of the aiming beam impingement—or on similar observations of a lack of balloon contact with blood in the vicinity of the aiming beam impingement. The aiming beam can, thereby, be used to determine the topography of the cardiac tissue at a candidate site, assess the quality of contact and/or lack of blood occlusion. Coupled with endoscopic observation of lesions as they are formed, the aiming beam can further be used to predict the path of future therapy and "line-up" the next candidate site to ensure the formation of contiguous (overlapping) spot ablations and, ultimately, a continuous vein-encircling lesion.

Endoscopic observation can also be used to select a dose for forming a spot lesion based on endoscopic observation following expansion of the expandable member and positioning of the energy emitter. For example, a dose can be selected based on an observed size of an impingement spot of an aiming beam or based on an observed balloon location.

The methods of the present invention can further include forming a first spot lesion and then repositioning the energy emitter to a second location. Next, visualization can be used to verify a second candidate site is acceptable for ablation by endoscopic observation of a aiming beam during repositioning of the energy emitter. Such visualization of observation can further be used to determine that a second (or subsequent candidate site) is suitable to forming a subsequent lesion that will be contiguous with the first lesion.

The endoscopes of the present invention can also be used in conjunction with other optical reflectance measurements of light scattered or absorbed by blood, body fluids and tissue. For example, white light projected by an illumination source toward tissue has several components including red and green light. Red light has a wavelength range of about 600 to about 700 nanometers (nm) and green light has a wavelength range of about 500 to about 600 nm. When the projected light encounters blood or body fluids, most if not all green light is absorbed and hence very little green or blue light will be reflected back toward the optical assembly which includes a reflected light collector. As the apparatus is positioned such that blood and body fluids are removed from the treatment field cleared by an inflated balloon member, the reflectance of green and blue light increases as biological tissue tends to reflect more green light. As a consequence, the amount of reflected green or blue light determines whether there is blood between the apparatus and the tissue or not.

Thus, the endoscopic displays of the present invention can incorporate filters (or generate "false-color" images) that emphasize the presence or absence of blood in the field. For example, when the inflated balloon member contacts the heart tissue (or is close enough that the balloon and ablative fluid released by the instrument form a clear transmission pathway), more green light will be reflected back into the optical assembly and the collector. The ratio of two or more different wavelengths can be used to enhance the image. Accordingly, a color-enhanced endoscope can permit visualization of the instrument and/or the target site, as well as a determination of whether blood precludes the formation of a continuous lesion, e.g., circumferential lesion around the ostium of a pulmonary vein.

Alternatively, spectrographic measurements can be taken in tandem with endoscopic imaging, Thus, reflected light can be transmitted back through a collector, such as an optical fiber to a spectrophotometer. The spectrophotometer (Ocean Optics Spectrometer, Dunedin, Fla., model S-2000) produces a spectrum for each reflected pulse of reflected light. Commercially available software (LabView Software, Austin, Tex.) can isolate values for specific colors and perform ratio analyses.

Once the operator is satisfied with the positioning of the instrument, radiant energy can then be projected to the target tissue region. If the radiant energy is electromagnetic radiation, e.g., laser radiation, it can be emitted onto the tissue site via a separate optical fiber or, alternatively, through the same optical fiber used for transmitting the white, green or red light. The laser light can be pulsed intermittently in synchronous fashion with the positioning/reflecting light to ensure that the pathway remains clear throughout the procedure.

In FIG. 17, a translatory mechanism 80 is shown for controlled movement of a radiant energy emitter within the instruments of the present invention. The exemplary positioner 80 is incorporated into a handle 84 in the proximal region of the instrument, where the elongate body 82 of the radiant energy emitter 40 engages a thumb wheel 86 to control advancement and retraction of the emitter. It should be clear that various alternative mechanisms of manual or automated nature can be substituted for the illustrated thumb wheel 86 to position the emitter at a desired location relative to the target tissue region.

In addition, as shown in FIG. 17, the elongate body 82 that supports the radiant energy emitter 40 can further include position indicia 92 on its surface to assist the clinician in placement of the ablation element within the instrument. The handle can further include a window 90 whereby the user can read the indicia (e.g., gradation markers) to gauge how far the emitter has been advanced into the instrument.

The assembly 32 can further include an endoscope translatory mechanism 98 as shown in FIG. 17 for controlled movement of the reflectance sensor or endoscope 76 within the instruments of the present invention. The exemplary positioner 98 can be incorporated into a handle 99 in the proximal region of the instrument, where the elongate body of the sensor 76 engages a thumb wheel 97 to control advancement and retraction of the emitter.

The apparatus of the present invention thus permits the selection of an ablative lesion, e.g., a circumferential lesion, of desired shape and size. This adjustability can be used advantageously to form a lesion at a desired location, or along a desired path, to effectively block conduction and thereby treat atrial fibrillation.

Although described in connection with cardiac ablation procedures, it should be clear that the instruments of the present invention can be used for a variety of other procedures where treatment with radiant energy is desirable, including laparoscopic, endoluminal, perivisceral, endoscopic, thoracoscopic, intra-articular and hybrid approaches.

The term "radiant energy" as used herein is intended to encompass energy sources that do not rely primarily on conductive or convective heat transfer. Such sources include, but are not limited to, acoustic and electromagnetic radiation sources and, more specifically, include microwave, x-ray, gamma-ray, ultrasonic and radiant light sources. The term "light" as used herein is intended to encompass electromagnetic radiation including, but not limited to, visible light, infrared and ultraviolet radiation.

The term "continuous" in the context of a lesion is intended to mean a lesion that substantially blocks electrical conduction between tissue segments on opposite sides of the lesion. The terms "circumferential" and/or "curvilinear," including derivatives thereof, are herein intended to mean a path or line which forms an outer border or perimeter that either partially or completely surrounds a region of tissue, or separate one region of tissue from another. Further, a "circumferential" path or element may include one or more of several shapes, and may be for example, circular, annular, oblong, ovular, elliptical, semi annular, or toroidal.

The term "lumen," including derivatives thereof, in the context of biological structures, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchoscopes, endoscopes, cystoscopes, culpascopes, colonscopes, trocars, laparoscopes and the like. Catheters of the present invention can be constructed with biocompatible materials known to those skilled in the art such as silicone rubber, polyethylene, Teflon, polyurethanes, nylon, polycarbonate, including blends and copolymers such PEBAX, etc.

The term "lumen" including derivatives thereof, in the context of catheters is intended to encompass any passageway within a catheter instrument (and/or track otherwise joined to such instrument that can serve as a passageway) for the passage of other component instruments or fluids or for delivery of therapeutic agents or for sampling or otherwise detecting a condition at a remote region of the instrument. The term "catheter" is also intended to encompass any elongate body capable of serving as a conduit for one or more of the ablation, expandable or sensing elements described herein, e.g., energy emitters, balloons and/or endoscopes. Specifically in the context of coaxial instruments, the term "catheter" can encompass either the outer catheter body or sheath or other instruments that can be introduced through such a sheath. The use of the term "catheter" should not be construed as meaning only a single instrument but rather is used to encompass both singular and plural instruments, including coaxial, nested and other tandem arrangements.

The term "vessel" or "blood vessel" includes, without limitation, veins, arteries, and various chambers or regions of the heart, such as the atria, ventricles, coronary sinus, vena cava and, in particular, the ostia or antrum of the pulmonary veins.

It should be understood that the term "balloon" encompasses deformable hollow shapes which can be inflated into various configurations including spherical, obloid, tear drop, etc., shapes dependent upon the requirements of the body cavity. Such balloon elements can be elastic or simply capable of unfolding or unwrapping into an expanded state. The balloon can further encompass multiple chamber configurations.

The term "transparent" is well recognized in the art and is intended to include those materials which allow transmission of energy through, for example, the primary balloon member.

Preferred transparent materials do not significantly impede (e.g., result in losses of over 20 percent of energy transmitted) the energy being transferred from an energy emitter to the tissue or cell site. Suitable transparent materials include fluoropolymers, for example, fluorinated ethylene propylene (FEP), perfluoroalkoxy resin (PFA), polytetrafluoroethylene (PTFE), and ethylene-tetrafluoroethylene (ETFE) or polyester resins including polyethylene teraphathalate (PET).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cardiac tissue ablation system, comprising:
   an elongate catheter that is formed of a material that is substantially transparent to radiant energy and is configured to deliver a distal end thereof to a patient's heart;
   an expandable member having a distal end that is attached to the distal portion of the catheter and a proximal end that is attached to a proximal portion of the catheter, the expandable member being substantially transparent to radiant energy and having an elastic portion configured to conform to the shape of a target tissue region upon expansion; and
   an energy emitter assembly movably disposed within a lumen of the catheter such that the energy emitter assembly is surrounded by the catheter and a point of attachment between the expandable member and the distal portion of the catheter is distal to the energy emitter, the energy emitter assembly including an energy emitter that is configured to deliver a series of arc-shaped spots of radiant ablative energy through the material that forms the catheter and the expandable member to the target tissue region, wherein a distal end of the energy emitter includes a plurality of beveled faces that converge to define an energy emitting face at a distal tip of the energy emitter, the energy emitting face being of reduced cross-section relative to a proximal portion of the energy emitter so as to provide an arc-shaped exposure pattern upon impingement with the target tissue region;
   wherein the beveled energy emitting face of the energy emitter is rectangular and is offset from an optical axis of a lens such that the radiant ablation energy is projected as an arc shaped beam.

2. The system of claim 1, wherein the energy emitter assembly is configured such that the spots of energy result in a series of lesions formed in the target tissue region when the emitter is activated, the lesions having an average area ranging from about 5 mm$^2$ to about 100 mm$^2$.

3. The system of claim 2, wherein the energy emitter is configured to form arc shaped lesions in the target tissue region subtending an angle ranging from about 5 degrees to about 45 degrees relative to the emitter so as to cause the radiant ablative energy to be forward projected relative to a perpendicular axis that intersects the energy emitter at a 90° degree angle relative to a longitudinal axis of the energy emitter.

4. The system of claim 2, wherein the energy emitter assembly is configured to form arc shaped lesions in the target tissue region subtending an angle of less than about 30 degrees relative to the emitter.

5. The system of claim 1, wherein the energy emitter assembly is slidably and rotatably disposed within an inner lumen of the catheter thereby allowing the energy emitter to effectively ablate any of a plurality of regions within the target tissue area.

6. The system of claim 1, wherein the energy emitter assembly is configured to project energy toward the target tissue area at an angle ranging from about 5 degrees to about 110 degrees relative to a longitudinal axis of the catheter.

7. The system of claim 6, wherein the energy emitter assembly includes a reflector element coupled to a distal end of the energy emitter.

8. The system of claim 7, wherein the reflector element is a quartz reflector.

9. The system of claim 1, wherein the energy emitter assembly is configured to project energy toward the target tissue area at an angle ranging from about 60 to about 90° degrees relative to a longitudinal axis of the catheter.

10. The system of claim 1, wherein the energy emitter comprises assembly includes an optic fiber with the lens coupled to a distal end of the fiber, the energy emitter assembly further having a reflector element positioned distal of the grins lens, the reflector element configured to deliver ablative energy to the cardiac tissue at an angle of about 90° relative to a longitudinal axis of the catheter.

11. The system of claim 10 that further includes at least one radiopaque marker visible via x-ray imaging shaped in such a manner as to allow the determination of the rotational orientation of the expandable member relative to the patients anatomy.

12. The system of claim 11 wherein the radiopaque marker resides at a known location relative to the view seen in the endoscope such that the orientation of the patients anatomy relative to the endoscopic view may be determined.

13. The system of claim 1, further including an endoscope configured to allow direct visualization of the tissue treatment area.

14. The system of claim 1, wherein the expandable member includes a plurality of markers defining a number of power-level segments, each power-level segment corresponding to an amount of ablation energy to be delivered to the segment by the energy emitter.

15. The system of claim 1, wherein the expandable member is a blunt-nosed balloon configured to impede passage of the balloon into a pulmonary vein when the balloon is deployed in proximity to the vein.

16. The system of claim 1, wherein the expandable member is a balloon with a tapered distal end that impedes passage of the balloon into a pulmonary vein when the balloon is deployed in proximity to the vein.

17. The system of claim 1 wherein the expandable member is a balloon whose distal portion gradually decreases in diameter.

18. A cardiac tissue ablation system, comprising:
   an elongate catheter that is formed of a material that is substantially transparent to radiant energy and is configured to deliver a distal end thereof to a patient's heart;
   an expandable member having a distal end that is attached to the distal portion of the catheter and a proximal end that is attached to a proximal portion of the catheter, the expandable member being substantially transparent to radiant energy and having an elastic portion configured to conform to the shape of a target tissue region upon expansion; and
   an energy emitter assembly movably disposed within a lumen of the catheter such that the energy emitter assembly is surrounded by the catheter and a point of attachment between the expandable member and the distal portion of the catheter is distal to the energy emitter, the energy emitter assembly including an energy emitter that is configured to deliver a series of arc-shaped spots of radiant ablative energy through the material that forms the catheter and the expandable member to the target tissue region, wherein a distal end of the energy emitter includes a plurality of beveled faces that converge to define an energy emitting face at a distal tip of the energy emitter, the energy emitting face being of reduced cross-section relative to a proximal portion of the energy emitter so as to provide an arc-shaped exposure pattern upon impingement with the target tissue region;

wherein the energy emitter assembly further comprises a lens configured to receive radiant energy from the energy emitting face of the optical fiber and focus the energy prior to passing through the expandable member, the lens being disposed distal to the energy emitting face of the optical fiber and the energy emitting face of the optical fiber and the lens being configured and arranged such that light propagating through the lens is bent into an arc-shaped exposure pattern.

* * * * *